(12) United States Patent
Byerly et al.

(10) Patent No.: US 11,554,221 B2
(45) Date of Patent: Jan. 17, 2023

(54) DOSE DETECTION MODULE FOR A MEDICATION DELIVERY DEVICE

(71) Applicant: Eli Lilly and Company, Indianapolis, IN (US)

(72) Inventors: Roy Howard Byerly, Indianapolis, IN (US); Rossano Massari, Lissone (IT); Davide Paccioretti, Samarate (IT)

(73) Assignee: Eli Lilly and Company, Indianapolis, IN (US)

( * ) Notice: Subject to any disclaimer, the term of this patent is extended or adjusted under 35 U.S.C. 154(b) by 893 days.

(21) Appl. No.: 16/317,251

(22) PCT Filed: Jul. 7, 2017

(86) PCT No.: PCT/US2017/041081
§ 371 (c)(1),
(2) Date: Jan. 11, 2019

(87) PCT Pub. No.: WO2018/013419
PCT Pub. Date: Jan. 18, 2018

(65) Prior Publication Data
US 2021/0330891 A1    Oct. 28, 2021

Related U.S. Application Data

(60) Provisional application No. 62/466,658, filed on Mar. 3, 2017, provisional application No. 62/362,808, filed on Jul. 15, 2016.

(51) Int. Cl.
*A61M 5/315* (2006.01)
(52) U.S. Cl.
CPC .... *A61M 5/31568* (2013.01); *A61M 5/31551* (2013.01); *A61M 5/31585* (2013.01);
(Continued)

(58) Field of Classification Search
CPC .......... A61M 5/31568; A61M 5/31551; A61M 5/31585; A61M 2205/3306
See application file for complete search history.

(56) References Cited

U.S. PATENT DOCUMENTS 6,277,099 B1    8/2001    Strowe et al.
8,560,271 B2    10/2013   Koehler et al.
(Continued)

FOREIGN PATENT DOCUMENTS

EP    2692378    2/2014
WO    9009202    8/1990
(Continued)

OTHER PUBLICATIONS

International Search Report of the International Searching Authority pertaining to International Application No. PCT/US2017/041081; International Filing Date: Jul. 7, 2017; dated Oct. 17, 2017.
(Continued)

*Primary Examiner* — Jenna Zhang
(74) *Attorney, Agent, or Firm* — M. Daniel Spillman

(57) ABSTRACT

The present disclosure relates to a dose detection system and method for a medication delivery device. The dose detection system may include a dosing component attached to an actuator and rotationally and axially moveable relative to a coupling component attached to a dose setting member. The dose detection system may further comprise a module including an electronic sensor operative to detect a relative rotation of the coupling component and the dosing component to detect a dose delivered by the medication delivery device.

29 Claims, 20 Drawing Sheets

(52) U.S. Cl.
CPC .............. *A61M 2205/3306* (2013.01); *A61M 2205/3327* (2013.01)

(56) References Cited

U.S. PATENT DOCUMENTS

| | | |
|---|---|---|
| 9,526,842 B2 | 12/2016 | Oh et al. |
| 9,561,332 B2 | 2/2017 | Butler et al. |
| 2002/0079200 A1 | 6/2002 | Juret et al. |
| 2004/0210199 A1 | 10/2004 | Atterbury et al. |
| 2008/0140018 A1 | 6/2008 | Enggaard et al. |
| 2008/0173522 A1 | 7/2008 | Asada |
| 2010/0286612 A1 | 11/2010 | Cirillo et al. |
| 2011/0270214 A1 | 11/2011 | Jørgensen et al. |
| 2011/0313349 A1* | 12/2011 | Krulevitch .............. A61M 5/24 604/65 |
| 2012/0053527 A1 | 3/2012 | Cirillo et al. |
| 2013/0123685 A1 | 5/2013 | Jespersen et al. |
| 2014/0074041 A1 | 3/2014 | Pedersen et al. |
| 2014/0163474 A1 | 6/2014 | Draper et al. |
| 2014/0194825 A1 | 7/2014 | Nielsen et al. |
| 2014/0194829 A1 | 7/2014 | Baek et al. |
| 2014/0312074 A1 | 10/2014 | Madsen et al. |
| 2015/0202376 A1 | 7/2015 | Haupt |
| 2015/0202377 A1 | 7/2015 | Haupt |
| 2015/0290396 A1 | 10/2015 | Nagar et al. |
| 2015/0343152 A1 | 12/2015 | Butler et al. |
| 2015/0352287 A1 | 12/2015 | Mercer et al. |
| 2015/0352289 A1 | 12/2015 | Mercer et al. |
| 2015/0352290 A1 | 12/2015 | Steel et al. |
| 2015/0356273 A1 | 12/2015 | Cave |
| 2015/0367077 A1 | 12/2015 | Plambech et al. |
| 2015/0367079 A1 | 12/2015 | Steel et al. |
| 2016/0015903 A1* | 1/2016 | Madsen ............ A61M 5/31568 604/211 |
| 2018/0154086 A1* | 6/2018 | Toporek ............ A61M 5/31551 |

FOREIGN PATENT DOCUMENTS

| | | | |
|---|---|---|---|
| WO | 9316743 | 9/1993 | |
| WO | 9524233 | 9/1995 | |
| WO | 9619872 | 6/1996 | |
| WO | 2009062675 | 5/2009 | |
| WO | 2010098927 | 9/2010 | |
| WO | 2011064299 | 6/2011 | |
| WO | 2012046199 | 4/2012 | |
| WO | 2013098421 | 7/2013 | |
| WO | 2014111340 | 7/2014 | |
| WO | 2014128155 | 8/2014 | |
| WO | 2014128156 | 8/2014 | |
| WO | 2014161952 | 10/2014 | |
| WO | 2014180744 | 11/2014 | |
| WO | 2014180745 | 11/2014 | |
| WO | 2015001008 | 1/2015 | |
| WO | 2015047870 | 4/2015 | |
| WO | 2015075134 | 5/2015 | |
| WO | 2015075135 | 5/2015 | |
| WO | 2015075136 | 5/2015 | |
| WO | WO-2015075134 A1 * | 5/2015 | .............. A61M 5/31 |
| WO | 2015138093 | 9/2015 | |
| WO | 2016131713 | 8/2016 | |
| WO | 2016180873 | 11/2016 | |
| WO | 2016193229 | 12/2016 | |
| WO | 2016198516 | 12/2016 | |
| WO | 2017009102 | 1/2017 | |
| WO | 2017108312 | 6/2017 | |
| WO | 2017114768 | 7/2017 | |

OTHER PUBLICATIONS

Written Opinion of the International Searching Authority pertaining to International Application No. PCT/US2017/041081; International Filing Date: Jul. 7, 2017; dated Oct. 17, 2017.

* cited by examiner

DOSE DETECTION MODULE FOR A MEDICATION DELIVERY DEVICE

TECHNICAL FIELD

The present disclosure relates to an electronic dose detection module for a medication delivery device, and more particularly to an electronic dose detection module adapted to removably attach to a proximal end portion of a medication delivery device to detect a dose of medication delivered by the delivery device.

BACKGROUND

Patients suffering from various diseases must frequently inject themselves with medication. To allow a person to conveniently and accurately self-administer medicine, a variety of devices broadly known as injector pens or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user, who then begins using a new replacement pen, discards the entire pen. In reusable pens, after a pen has been utilized to exhaust the supply of medication within the cartridge, the pen is disassembled to allow replacement of the spent cartridge with a fresh cartridge, and then the pen is reassembled for its subsequent use.

Most injector pens and other medication delivery devices do not include the functionality to automatically detect and record the amount of medication delivered by the device to the patient during the injection event. Rather, a patient must manually keep track of the dose amount and time of each injection. Accordingly, there is a need for a device that is operative to automatically detect the dose delivered by the medication delivery device during each injection event. Further, there is a need for such a dose detection device to be removable and reusable with multiple delivery devices.

SUMMARY

In a first aspect of the present disclosure, a medication delivery device is provided in which the amount of a dose delivery is determined based on the relative rotation of a dose setting member during dose delivery. The device comprises a device body, a dose setting member rotatably attached to the device body, and an actuator attached to the device body. The actuator and the dose setting member rotate and translate together during dose setting. The actuator translates axially without rotation during dose delivery, and the dose setting member rotates relative to the actuator in relation to the amount of dose delivered. The device further includes a coupling component attached to rotate and translate with the dose setting member. A dosing component rotates and translates with the coupling component during dose setting, and is rotationally fixed to the actuator during dose delivery. The amount of dose delivery is determined from the rotation of the coupling component relative to the dosing component during dose delivery.

In accordance with a second aspect of the present disclosure, a dose detection module is provided for attachment to a medication delivery device. The dose detection module includes a coupling component comprising a first housing portion and a dosing component comprising a second housing portion coupled to the first housing portion. The first housing portion includes a coupling wall and a coupling member. The coupling member is configured to removably couple to a dose setting member of the medication delivery device. The second housing portion is configured to engage an actuator member of the medication delivery device and includes an inner wall radially offset from the coupling wall. The inner wall and the coupling wall are rotatable relative to each other about an axis and axially moveable relative to each other along the axis. The dose detection module further includes an electronics assembly coupled to the second housing portion. The electronics assembly includes a rotation sensor operative to detect a relative rotation of the coupling wall and the inner wall.

Among other advantages in certain embodiments, an attachable and detachable dose detection module is provided that is operative to detect a delivered medication amount without changing the functionality or operation of the delivery device. In some embodiments, a same mechanical dose display is used by the user to view the selected dose during use of the delivery device with or without the module attached. In some embodiments, the sensing system, such as sliding contacts for example, of the module does not require sensor calibration by the end user. In some embodiments, mechanical keying plus color coding of the module to the delivery device allows for identification of a proper delivery device and/or medication. In some embodiments, redundant sensors are provided to add robustness to the dose sensing system. In some embodiments, the sensing system records the size of the delivered dose and monitors the elapsed time since the last dose. Other advantages will be recognized by those of ordinary skill in the art.

BRIEF DESCRIPTION OF THE DRAWINGS

The features and advantages of the present disclosure will become more apparent to those skilled in the art upon consideration of the following detailed description taken in conjunction with the accompanying figures, wherein.

DETAILED DESCRIPTION

Figure 1:
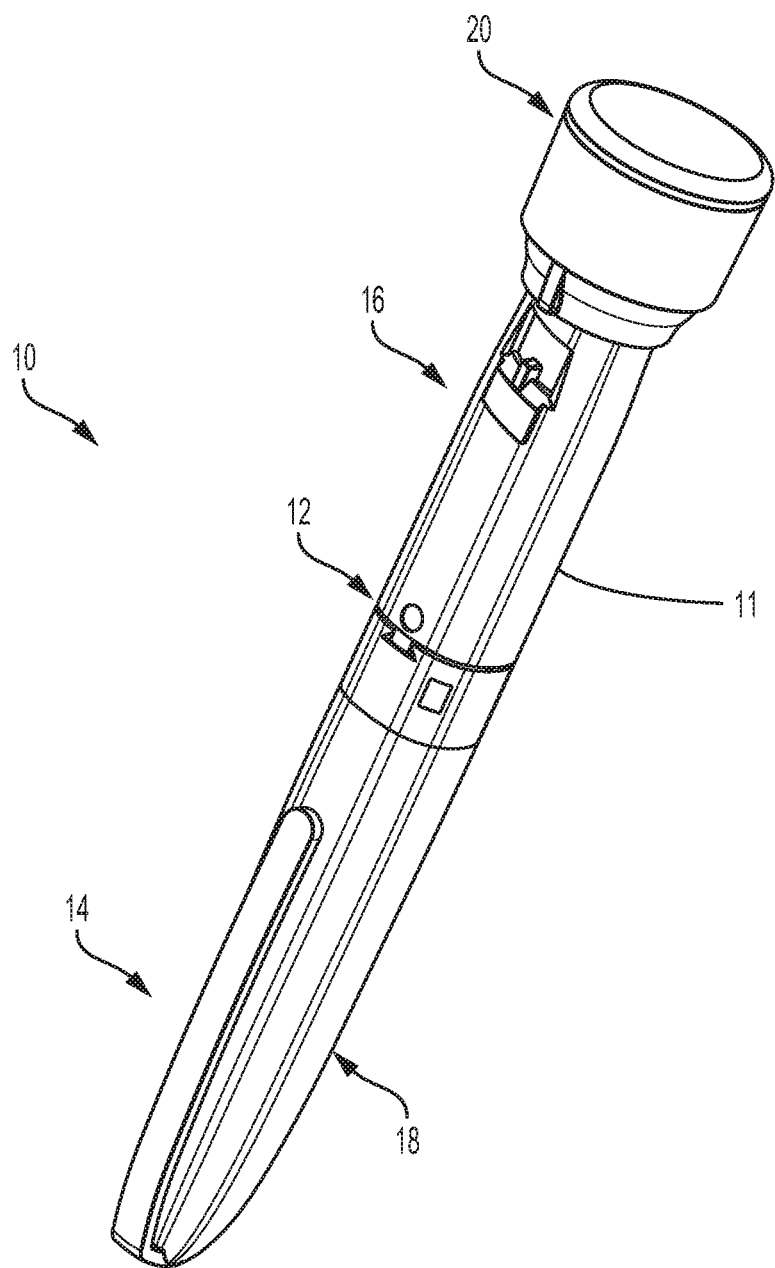
FIG. 1 is a perspective view of an exemplary dose detection module according to an illustrated embodiment coupled to a proximal end of a medication delivery device.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

FIG. 1 illustrates a dose detection module 20 coupled to a proximal end of a medication delivery device 10. Dose detection module 20 is removably attached to delivery device 10 in that a user may attach module 20 to and detach module 20 from the delivery device 10. For example, prior to dose setting and injecting with delivery device 10 (or in some embodiments of device 10 after dose setting and prior to injecting), a user may couple module 20 onto the end of device 10. Dose detection module 20 is operative to detect the amount of medication dispensed by delivery device 10 while attached to device 10, as described herein. Module 20 is further operative to store the detected dose in memory and transmit a signal representative of the detected dose to a remote communication device. After injecting the set dose with device 10 and detecting the delivered dose with module 20, the user may remove the module 20 and, in the illustrative embodiment, reuse the module 20 later with the same or a different delivery device 10 when performing another dose delivery.

Medication delivery device 10 is illustrated in FIG. 1 as an injector pen 10 having a device body 11 comprising an elongated, pen-shaped housing 12 and being configured to inject a medication into a patient through a needle. Other shapes and forms of delivery device 10, including devices that are not pen-shaped, may be provided for use with dose detection module 20, including any suitable needle or needleless delivery device. In one embodiment, delivery device 10 is a disposable or prefilled injector pen, in that after the quantity of medicine contained in a reservoir of the pen is exhausted by multiple operations of the pen, the entire pen is discarded rather than being reset and reloaded with a replacement container of medicine. Alternatively, delivery device 10 may be a reusable injector pen wherein after the quantity of medicine in the reservoir is exhausted by multiple operations of the pen, the empty container is removed from the pen and a replacement medicine container is loaded into the pen. Delivery device 10 is operable by a user to select and then inject any one of a number of different size doses, such as may be appropriate with some therapeutics loaded therein, for example insulin. Delivery device 10 is also adapted to deliver a dose in a specific amount appropriate for other suitable types of therapeutics loaded therein.

Figure 2:
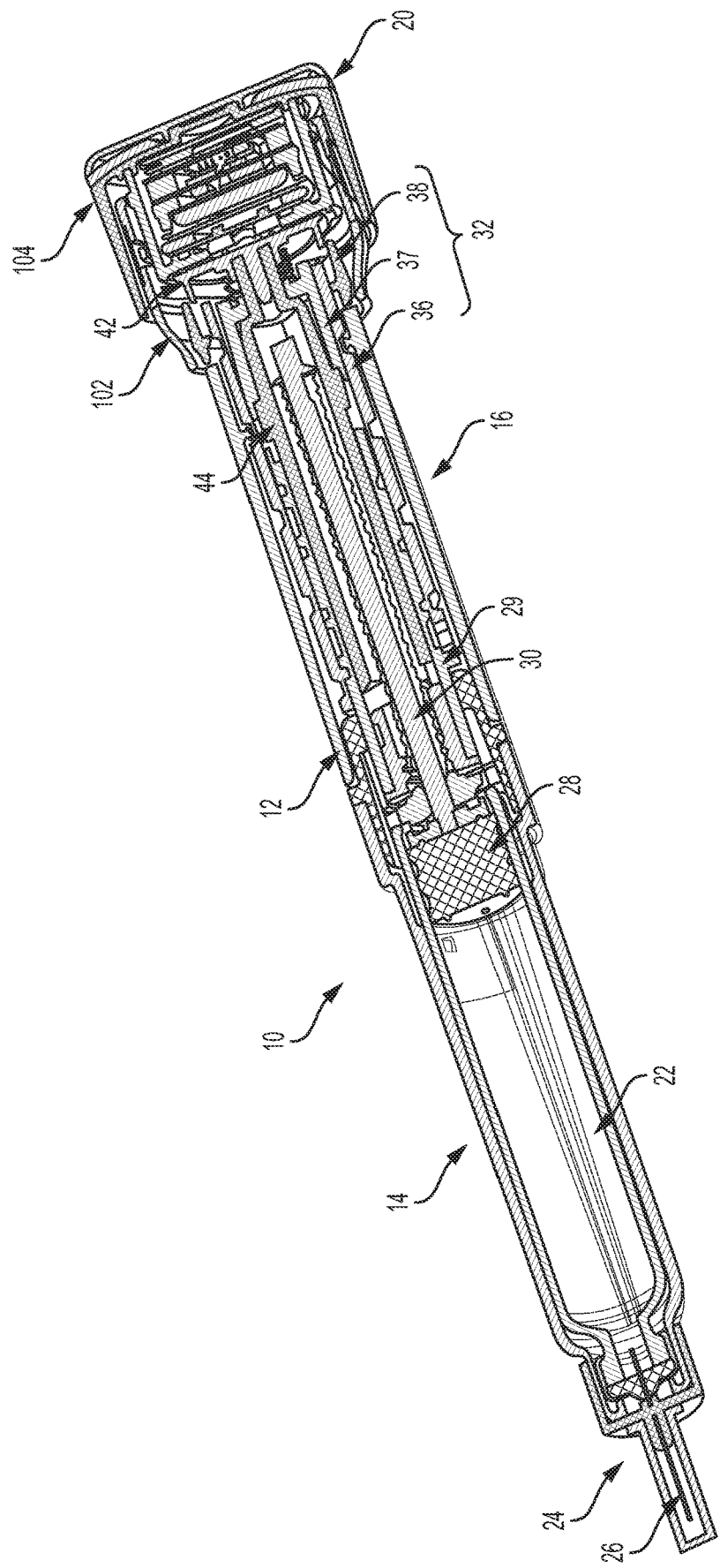
FIG. 2 is a cross-sectional perspective view of the dose detection module and medication delivery device of FIG. 1.

Housing 12 of delivery device 10 includes a distal portion 14, which is received within a pen cap 18, and a proximal portion 16. Referring to FIG. 2, distal portion 14 contains a reservoir or cartridge 22 configured to hold the medicinal fluid to be dispensed through its distal outlet end during a dispensing operation. The outlet end of distal portion 14 is equipped with a removable needle assembly 24 including an injection needle 26. A piston 28 is positioned in fluid reservoir 22. An injecting mechanism positioned in proximal portion 16 is operative to advance piston 28 towards the outlet of reservoir 22 during the dose dispensing operation to force the contained medicine through the needled end. The injecting mechanism includes a drive member 30, illustratively in the form of a screw, axially moveable relative to housing 12 to advance piston 28 through reservoir 22.

A dose setting member 32 is coupled to housing 12 for setting a dose amount to be dispensed by device 10. In the illustrated embodiment, dose setting member 32 is in the form of a screw element operative to screw (i.e., simultaneously move axially and rotationally) relative to housing 12 during dose setting and dose dispensing. FIGS. 1 and 2 illustrate the dose setting member 32 fully screwed into housing 12 at its home or zero position. Dose setting member 32 is operative to screw out in a proximal direction from housing 12 until it reaches a fully extended position corresponding to a maximum dose deliverable by device 10 in a single injection.

Referring to FIGS. 2-5, dose setting member 32 includes a cylindrical dial member 36 having a helically threaded outer surface that engages a corresponding threaded inner surface of housing 12 to allow dose setting member 32 to screw relative to housing 12. Dial member 36 further includes a helically threaded inner surface that engages a threaded outer surface of a sleeve 29 (FIG. 2) of device 10. In one embodiment, the outer surface of dial member 36 includes dose indicator markings, such as numbers for example, that are visible through a dosage window 40 to indicate to the user the set dose amount. Dose setting member 32 further includes a tubular flange 37 that is coupled in the open proximal end of dial member 36 and is axially and rotationally locked to dial member 36. Dose setting member 32 further includes a skirt or collar 38 positioned around the outer periphery of dial member 36 at its proximal end. Skirt 38 is axially and rotationally locked to dial member 36. Skirt 38 illustratively includes a plurality of surface features 39 formed on the outer surface of skirt 38. Surface features 39 are illustratively longitudinally extending ribs and grooves that are circumferentially spaced around the outer surface of skirt 38. An annular ridge 41 extends around the outer periphery of skirt 38 for attachment of dose detection module 20. The ribbed outer surface 39 and ridge 41 of skirt 38 cooperate to provide a keyed attachment to a coupling component 106 (FIG. 5) of dose detection module 20, as described herein.

Figure 3:
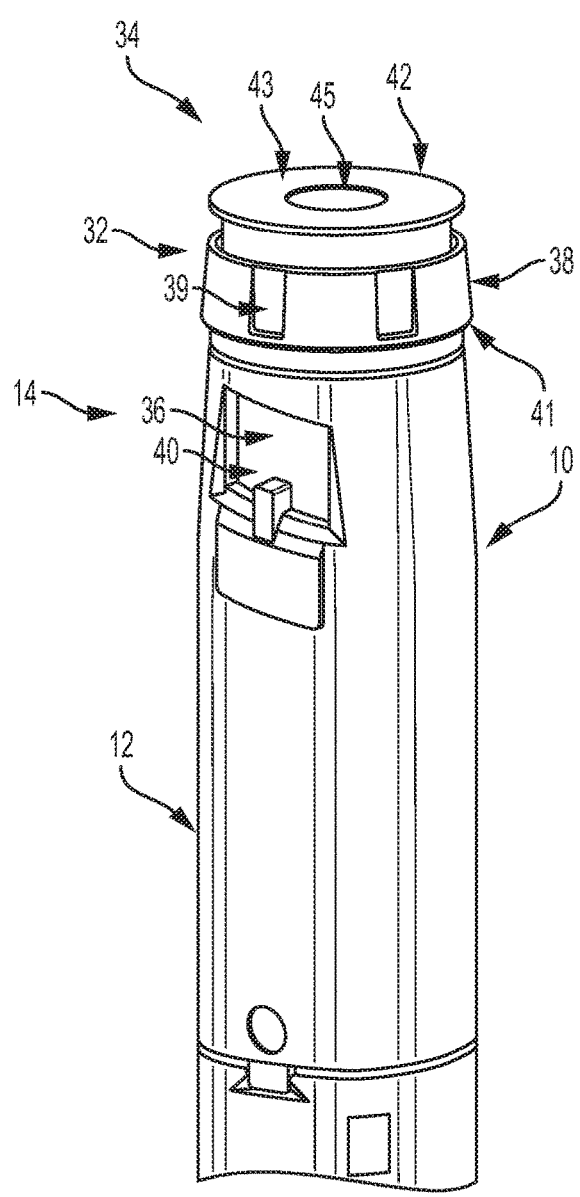
FIG. 3 is a perspective view of the proximal portion of the medication delivery device of FIG. 1.
Figure 4:
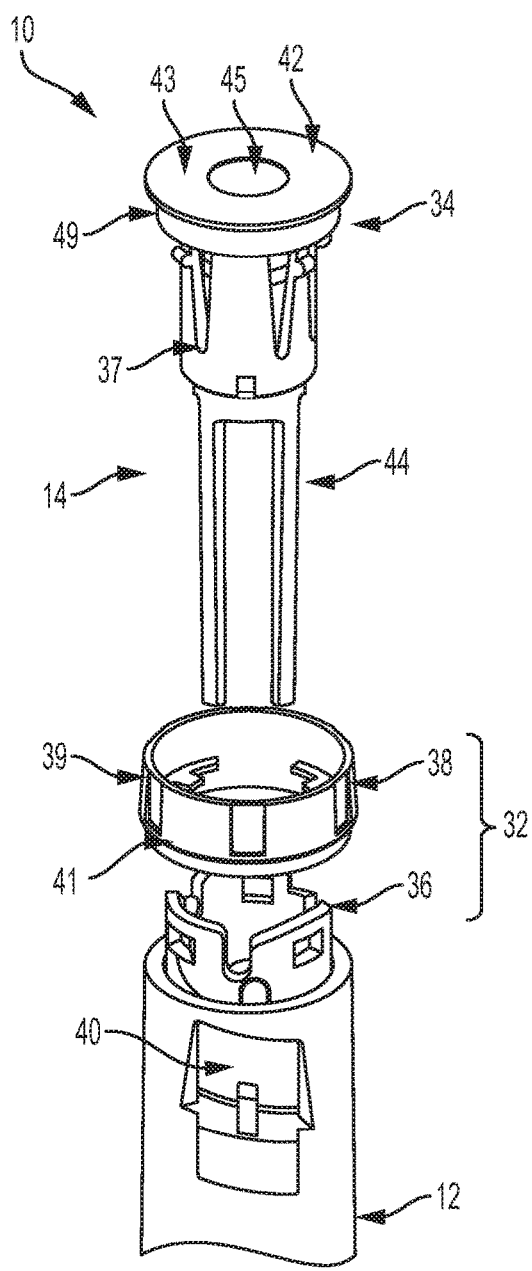
FIG. 4 is a partially exploded perspective view of the proximal portion of the medication delivery device of FIG. 1.
Figure 5:
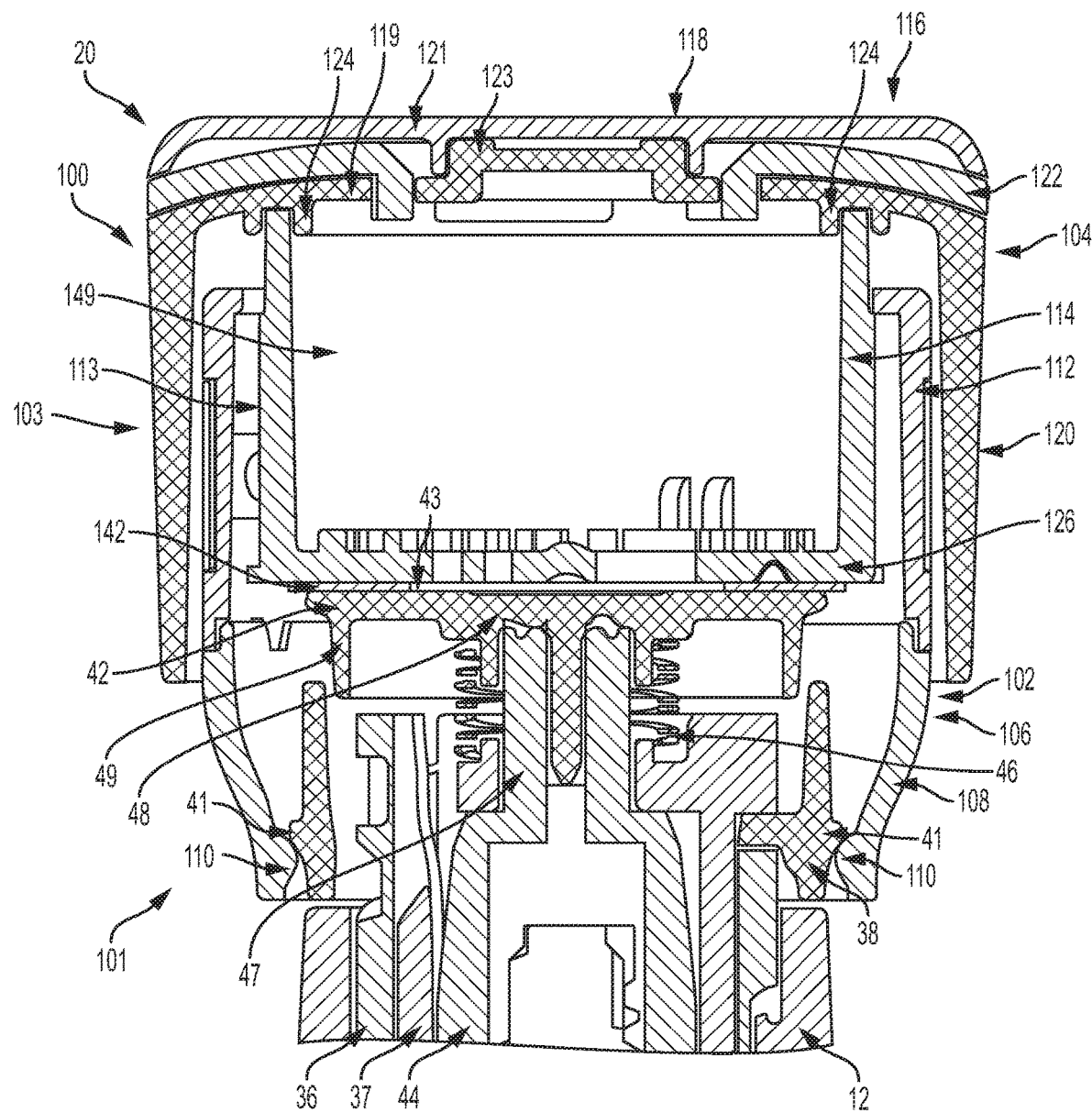
FIG. 5 is a cross-sectional view of the dose detection module of FIG. 1 attached to the proximal portion of the medication delivery device, with an electronics assembly of the dose detection module removed for illustrative purposes.
Figure 6:
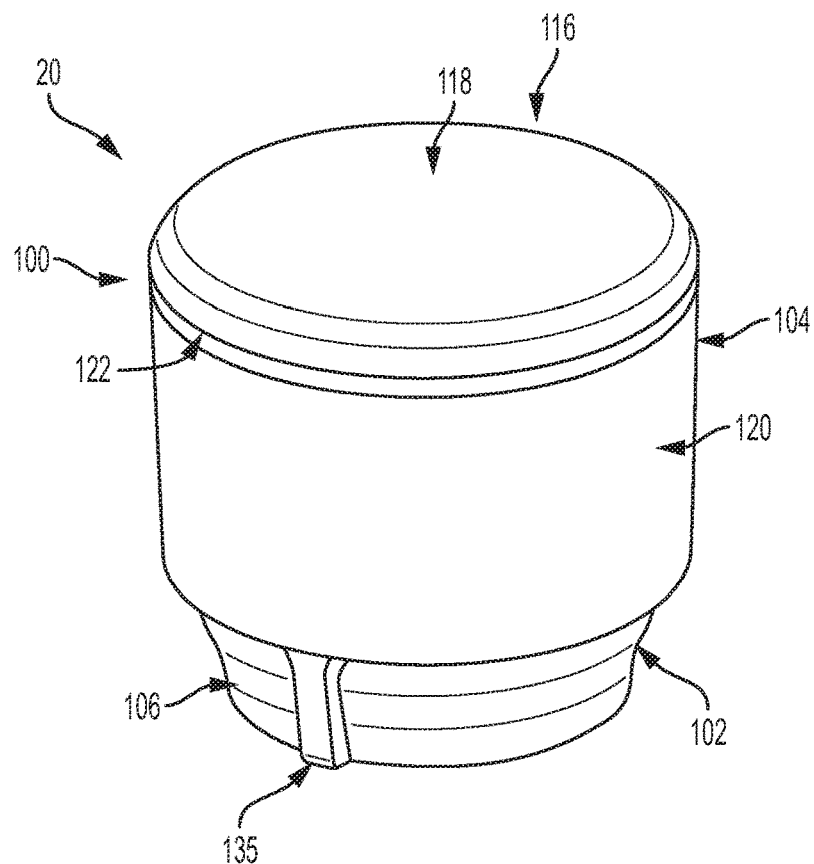
FIG. 6 is a side perspective view of a dose detection module of FIG. 1 removed from the delivery device.
Figure 7:
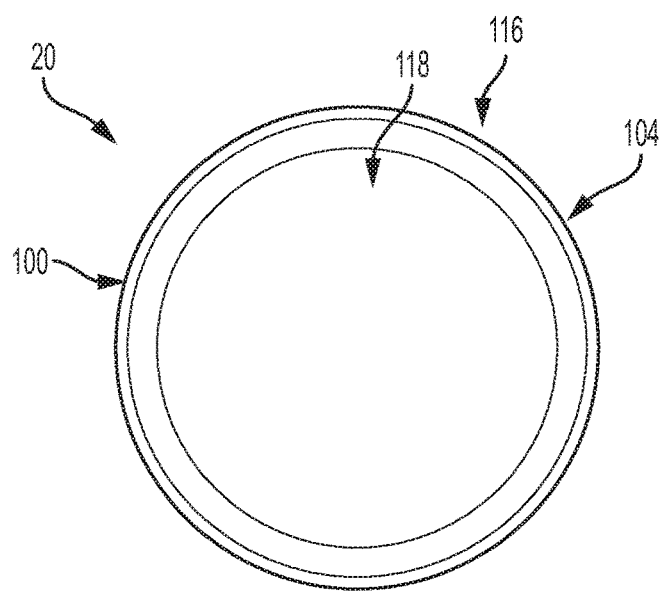
FIG. 7 is a top plan view of the dose detection module of FIG. 6.

Referring to FIGS. 3-5, an actuator 34 of delivery device 10 includes a clutch 44 which is received within dial member 36 and includes an axially extending stem 47 (FIG. 5) at its proximal end. Actuator 34 further includes a button 42 positioned proximally of dose setting member 32 that is depressible by a user to initiate the dose dispensing operation. Button 42 includes a disk-shaped proximal end surface or face 43 and an annular wall portion 49 extending from a distal surface and spaced radially inwardly of the outer peripheral edge of face 43 to form an annular lip there between. A mounting collar 48 (FIG. 5) is centrally located on the distal surface of button 42 within cylindrical wall portion 49. Button 42 illustratively includes a recessed portion 45 centrally located on proximal face 43, although proximal face 43 alternatively may be a flat surface. Proximal face 43 of button 42 serves as a push surface against which a force can be applied manually (i.e. directly by user contact or through dose detection module 20) to push actuator 34 in a distal direction. Collar 48 of button 42 is secured to stem 47 of clutch 44, such as with an interference fit or an ultrasonic weld, so as to axially and rotatably fix together button 42 and clutch 44. A bias member 46, illustratively a spring 46, is disposed between the distal surface of button 42 and the proximal surface of sleeve 36 to urge actuator 34 and dose setting member 32 axially away from each other.

Delivery device 10 is operable in a dose setting mode and a dose dispensing mode. In the dose setting mode of operation, the dose setting member 32 is screwed or dialed relative to housing 12 to set a desired dose to be delivered by device 10. Dialing in the proximal direction serves to increase the set dose, and dialing in the distal direction serves to decrease the set dose. Dose setting member 32 is adjustable in rotational increments (e.g., clicks) corresponding to the minimum incremental increase or decrease of the set dose during the dose setting operation (e.g., one increment or click equals, for example, one unit or a half unit of medication). The set dose amount is visible to the user via the dial indicator markings shown through dosage window 40. Actuator 34, including button 42 and clutch 44, move axially and rotationally with dose setting member 32 during the dialing in the dose setting mode.

Once the desired dose is set and after device 10 is manipulated so the injection needle 26 properly penetrates, for example, a user's skin, the dose dispensing mode of operation is initiated in response to an axial distal force applied to the proximal face 43 of button 42, which causes axial movement of actuator 34 in the distal direction (without rotation) relative to dose setting member 32 towards housing 12. The axial force is applied by the user directly to button 42 or to a dose detection module 20 attached to button 42. The axial shifting motion of actuator 34 compresses biasing member 46 and reduces or closes the gap between button 42 and tubular flange 37, thereby rotationally disengaging actuator 34 from dose setting member 32 (e.g., rotationally disengaging clutch 44 from tubular flange 37) to allow relative rotation there between. In particular, dose setting member 32 rotatably uncouples from actuator 34 to allow back driving rotation of dose setting member 32 relative to actuator 34. As actuator 34 is continued to be axially plunged without rotation by compression of button 42, dial member 36 screws back into housing 12 as it spins relative to button 42 and the dose markings that indicate the amount still remaining to be injected are visible through window 40. As dose setting member 32 screws down distally, drive member 30 is advanced distally to push piston 28 through reservoir 22 and expel medication through needle 26 (FIG. 2). During the dose dispensing operation, the amount of medicine expelled from the device is proportional to the amount of axial movement and to the amount of rotational movement of the dose setting member 32 as the dial member 36 screws back into housing 12. The injection is completed when the internal threading of dial member 36 has reached the distal end of corresponding outer threading of sleeve 29 (FIG. 2), at which time pen 20 is once again arranged in a ready state or zero dose position as shown in FIGS. 1 and 3.

Further details of the design and operation of an exemplary delivery device 10 may be found in U.S. patent application Ser. No. 10/567,196, filed Feb. 3, 2006 and entitled Medication Dispensing Apparatus with Triple Screw Threads for Mechanical Advantage, now U.S. Pat. No. 7,291,132, the entire disclosure of which is incorporated by reference herein.

Referring to FIGS. 5-10, dose detection module 20 includes a housing assembly 100 comprising a coupling component 101 including a first housing portion 102 and a dosing component 103 including a second housing portion 104 coupled to first housing portion 102. As described herein, first and second housing portions 102, 104 are rotatable relative to each other about a longitudinal axis and are axially moveable relative to each other along the axis. First housing portion 102 includes a coupling wall 112 (FIGS. 5, 9, 10), illustratively in the form of a cylinder 112, and a coupling member 106 fixed to a distal end of coupling wall 112. Coupling wall 112 and coupling member 106 may be fixed together via any suitable fastening means, such as a weld, snap fit, threaded interface, etc., or alternatively may be integrally formed as a single component. In the illustrative embodiment, coupling member 106 includes an annular ridge 131 that extends axially from the proximal end forming an annular shoulder 133 between ridge 131 and an outer surface 132 of coupling member 106 (see FIG. 9). The distal end of coupling wall 112 includes circumferentially spaced tabs 136 (FIG. 10) that snap fit into corresponding circumferentially spaced notches 134 formed in ridge 131 to rotationally and axially fix coupling member 106 to coupling wall 112. When coupled together, the distal end of coupling wall 112 abuts annular shoulder 133 of coupling member 106.

Coupling member 106 includes an annular ring portion 108 sized to receive dose setting member 32 and to engage an outer surface of dose setting member 32, illustratively skirt 38, for attaching first housing portion 102 to delivery device 10. As illustrated, outer surface 132 tapers radially inwardly from shoulder 133 to ring portion 108 such that a proximal end diameter of coupling member 106 is larger than a distal end diameter of coupling member 106. An inner surface 109 of ring portion 108 includes a plurality of surface features 110, illustratively variably sized projections and grooves, that are sized to engage corresponding surface features 39 (e.g., grooves) of skirt 38 for coupling thereto. In the illustrated embodiment, surface features 110 of coupling member 106 couple to annular ridge 41 of skirt 38 (FIG. 5) via a snap fit or an interference fit, although any other suitable fastening mechanism may alternatively be used to couple first housing portion 102 to dose setting member 32.

In the illustrative embodiment, surface features 110 and 39 are sized, shaped, and spaced to provide mechanical keying of dose detection module 20 to delivery device 10. In particular, in the illustrative embodiment, detection module 20 is mechanically keyed via surface features 110 to be compatible with a specific type or types of delivery devices having compatible surface features 39, such as based on medication type, concentration, strength, volume, and/or formulation, as well as cartridge size or other aspects of the corresponding delivery device. In some embodiments, electronics assembly 140 of module 20 is pre-programmed to operate based on the compatible delivery device(s) and/or medication. Such mechanical keying serves to reduce the likelihood that detection module 20 is used with an incorrect delivery device and/or medication. With the mechanical key feature, module 20 must be in proper rotational alignment with skirt 38 of device 10 to slide and snap coupling member 106 onto skirt 38. Coupling member 106 illustratively includes a projection 135 on its outer surface 132 that serves as a visual guide or reference for rotationally aligning module 20 to dose setting member 32. Other keying features, such as color coding, may be used to identify a correct module 20 for a corresponding delivery device 10.

Referring still to FIGS. 5-10, second housing portion 104 includes a drum 113 (FIGS. 5, 9, and 10) and a cap portion 116 coupled to a proximal end of drum 113. Drum 113 illustratively includes inner wall 114 and a disc-shaped base wall 126 at a distal end of inner wall 114. Inner wall 114 illustratively includes an upper wall portion 138 and a lower wall portion 139 having a greater outer diameter but a same inner diameter as upper wall portion 138, forming an annular ridge 141 on the outer surface of inner wall 114. Cap portion 116 includes an end wall 118 positioned orthogonally to circumferential wall 114. End wall 118 illustratively includes a distal wall portion 119 and a proximal wall portion 121 coupled to distal wall portion 119 at a centrally located mounting interface 123 via a snap fit, interference fit, ultrasonic weld, or other suitable coupling mechanism. Cap portion 116 further includes an outer wall 120 radially spaced apart from and substantially parallel to inner wall 114. In the illustrated embodiment, coupling wall 112 of first housing portion 102 is positioned in the gap formed radially between outer wall 120 and inner wall 114 of second housing portion 104. End wall 118 of cap portion 116 includes a mounting collar 124 (FIGS. 5 and 10) axially extending from and centrally located on distal wall portion 119. Upper wall portion 138 of inner wall 114 is fixed to mounting collar 124 via any suitable coupling mechanism, such as ultrasonic weld or interference fit for example.

In the illustrated embodiment, a ring-shaped indicator light 122 is integrated into end wall 118 between distal wall portion 119 and proximal wall portion 121. Indicator light 122 illustratively includes one or more light-pipes 144 illuminated by one or more light-emitting diodes (LEDs) of electronics assembly 140. Light pipe 144 is disc shaped and includes a centrally located mounting collar 145 that is coupled to slots 147 formed in distal wall portion 119 of end wall 118. Indicator light 122 is electronically controlled by a processor of electronics assembly 140 for providing visual feedback to a user of the operational state of detection module 20. For example, indicator lights 122 may illuminate in different colors based on module 20 being in particular power state, a dose detecting mode, a wireless transmitting mode, a faulted or error state, or any other suitable operational state. In an alternative embodiment, indicator lights 122 may also indicate to a user that module 20 is improperly attached to device 10.

Still referring to FIGS. 5-10, when module 20 is attached to delivery device 10, a distal surface of base wall 126 abuts proximal end surface 43 of button 42 (FIG. 4). Illustratively, the distal surface of base wall 126 includes a thin, disc-shaped friction pad 142 having a central opening. Pad 142 provides frictional resistance (e.g., via surface roughness and/or adhesive) between base wall 126 and button 42 such that second housing portion 104 remains rotationally coupled to button 42 during operation of module 20 with device 10. Base wall 126 of drum 113 in some embodiments may include a centrally located, axially extending projection (not shown) configured for receipt within recessed portion 45 of button 42, such as for coupling and/or alignment of button 42 and base wall 126.

Figure 8:
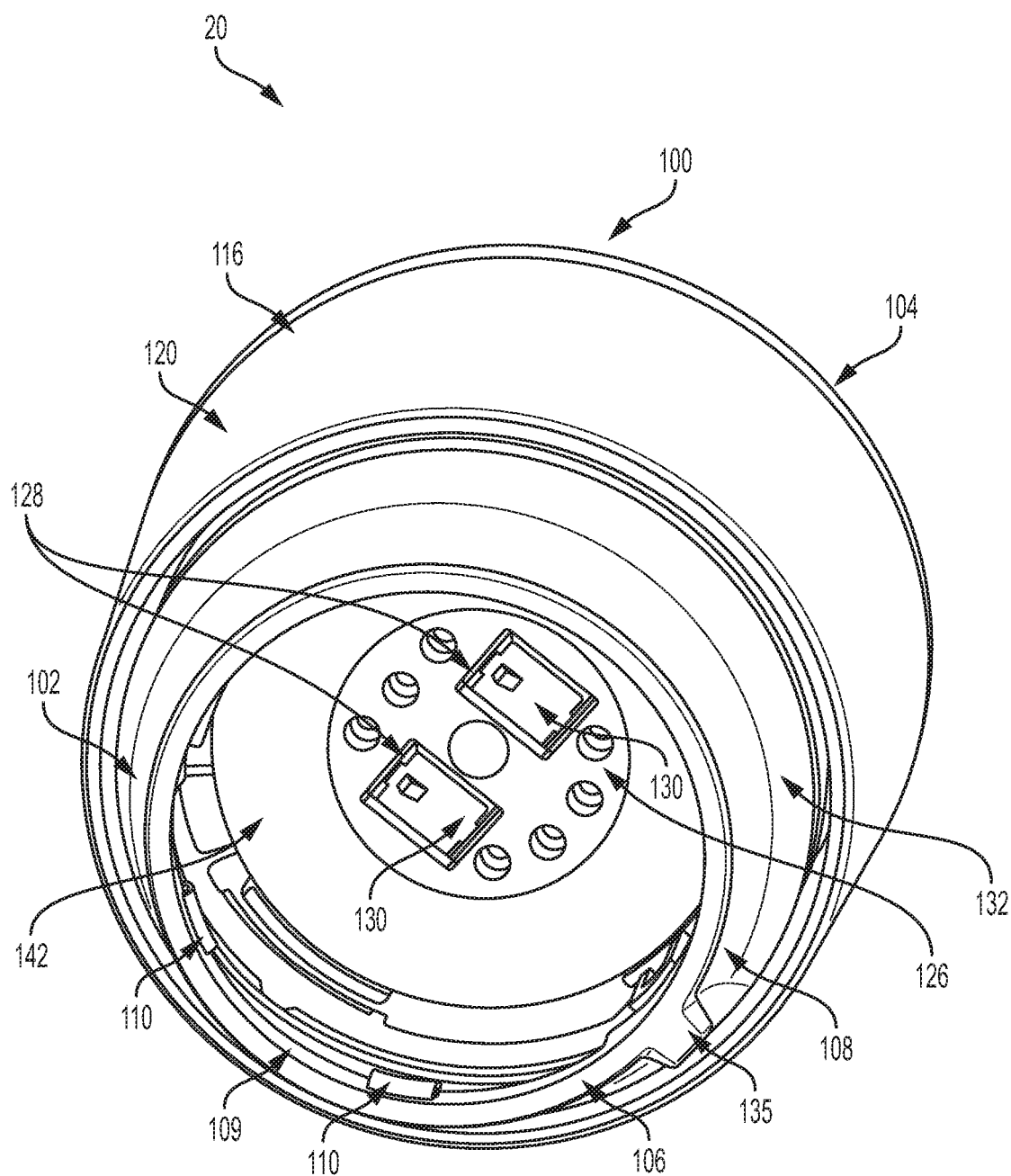
FIG. 8 is a bottom perspective view of the dose detection module of FIG. 6.
Figure 9:
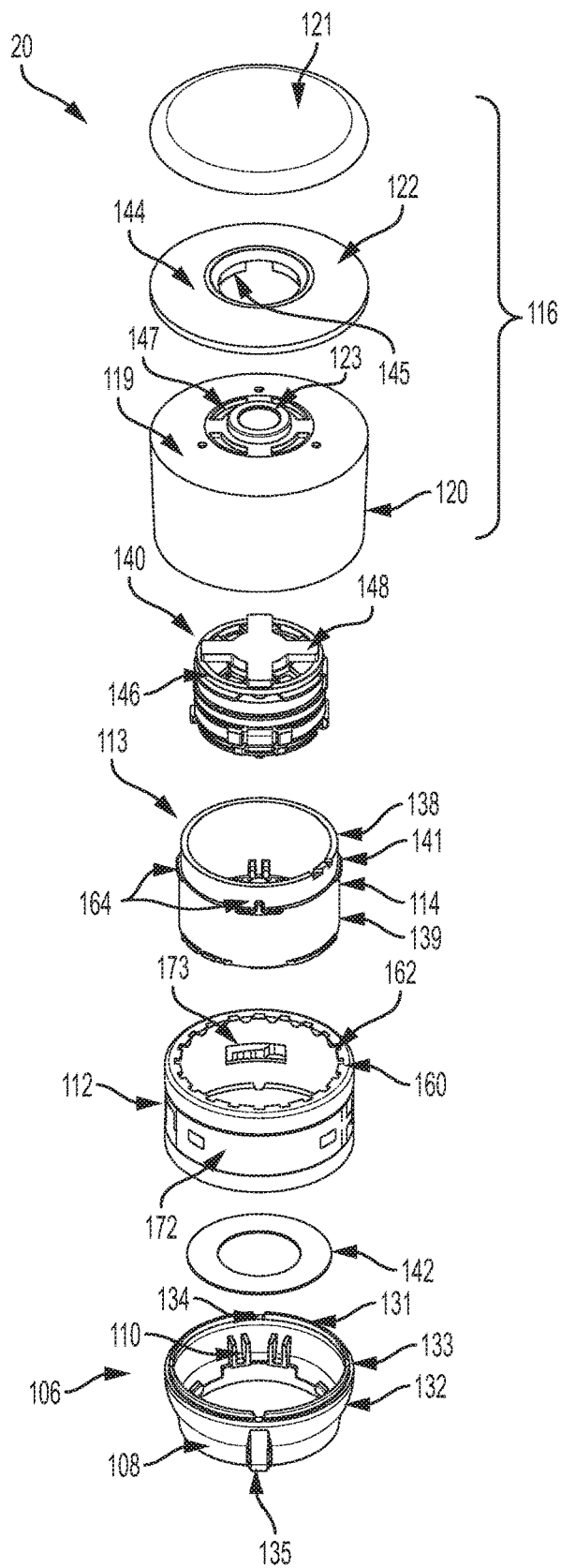
FIG. 9 is an exploded top perspective view of the dose detection module of FIG. 6.
Figure 10:
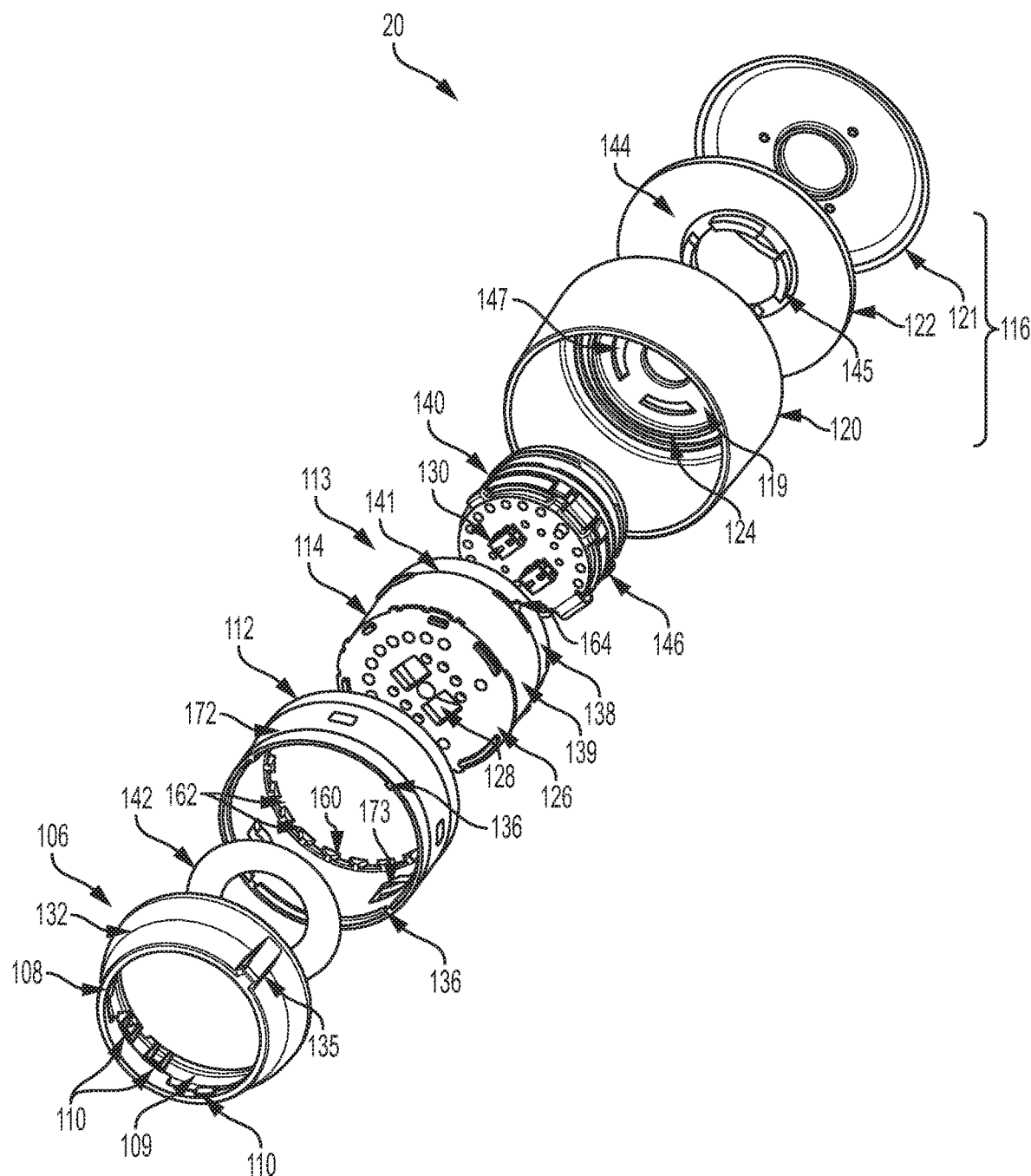
FIG. 10 is an exploded bottom perspective view of the dose detection module of FIG. 6.

As illustrated in FIGS. 8 and 10, centrally located apertures 128 are formed in base wall 126 for receiving electrical switches 130 of electronics assembly 140. Switches 130 are mechanically actuated or triggered by engagement with the proximal surface 43 of button 42. In the illustrative embodiment, electronics assembly 140 is operative to power on from a low power mode or powered off mode, or to enter a low power mode from a powered off mode, upon proper attachment of housing assembly 100 to button 42 based on actuation of switches 130, as described in greater detail herein. While two apertures 128 and two switches 130 are illustrated, any suitable number of apertures 128 and switches 130 may be provided and spaced appropriately on base wall 126 for detecting proper attachment of module 20 to delivery device 10.

In the illustrated embodiment, when dose detection module 20 is attached to delivery device 10, first and second housing portions 102, 104 and dose setting member 32 are coaxial and are thus operative to rotate together about a same longitudinal axis during a dose setting operation of delivery device 10. In addition, first and second housing portions are operative to move axially together with the dose setting member 32 along the longitudinal axis during the dose setting operation and axially relative to each other along the longitudinal axis in response to an axial force on second housing portion 104 to start the dose dispensing operation. While coupling wall 112 and inner wall 114 of respective first and second housing portions 102, 104 illustratively extend 360 degrees about the longitudinal axis of module 20, coupling wall 112 and inner wall 114 alternatively may extend a portion of the full circumference about the axis. In other words, walls 112, 114 may include one or more breaks in the respective wall somewhere along the perimeter rather than being continuous walls as illustrated.

Dose detection module 20 is configured for operation in at least a first operating mode and a second operating mode. In the illustrated embodiment, the first operating mode corresponds to the dose setting operation of delivery device 10, and the second mode corresponds to the dose dispensing operation of delivery device 10. In the first operating mode, first and second housing portions 102, 104 are at a home position axially wherein second housing portion 104 is not axially compressed relative to first housing portion 102. In this first mode, first and second housing portions 102, 104 are rotationally locked together by a locking mechanism, illustratively a tooth and slot coupling. Referring again to FIGS. 9 and 10, the proximal end of coupling wall 112 of first housing portion 102 includes a radially extending annular lip 160 having a plurality of circumferentially spaced slots 162 formed therein. Slots 162 of lip 160 are each sized to receive a tooth or tongue 164 formed on the outer surface of upper wall portion 138 of inner wall 114. Illustratively, four teeth 164 are spaced 90 degrees apart around upper wall portion 138, and twenty slots 162 are equally spaced around lip 160, although any suitable number of teeth 164 and slots 162 may be provided. In the illustrative embodiment, the number of slots 162 is the same as the number of rotational increments or clicks to which dose setting member 32 of device 10 may be set in one complete rotation of dial member 36 relative to housing 12. The multiple slots 162 allow first housing portion 102 and second housing portion 104 to lock together in the first mode in multiple relative rotational positions, with more slots 162 providing more possible relative positions. In an alternative embodiment, slots 162 may be formed on inner wall 114 and tongues formed on coupling wall 112. Other suitable rotational locking mechanisms may be provided.

In general, dosing component 103 has a first operating mode during dose setting in which the dosing component is axially and rotationally fixed to the coupling component. In this first mode, dosing component 103 may be grasped by the user and rotated relative to device body 11. Due to the connections between dosing component 103 and coupling component 101, and between coupling component 101 and dose setting member 32, the rotation of dosing component 103 results in rotation of dose setting member 32 and a dose is set. During dose setting, actuator 34, including dose button 42, is connected by way of clutch 44 to dose setting member 32 and spirals with dose setting member 32 relative to device body 11.

In one embodiment, dosing component 103 includes inner wall 114 and outer wall 120, and coupling component 101 includes coupling wall 112 received between the inner and outer walls. Dose setting member 32 includes an exposed circumferential surface, optionally including surface features 39, for use in rotating the dose setting member relative to the device body. Coupling wall 112 extends distally beyond inner wall 114 and includes a coupling portion attached to the exposed circumferential surface of the dose setting member in order to attach the coupling component 101 to the dose setting member 32. In another aspect, outer wall 120 extends distally to radially overlap at least a portion of the exposed circumferential surface of the dose setting member.

Figure 25:
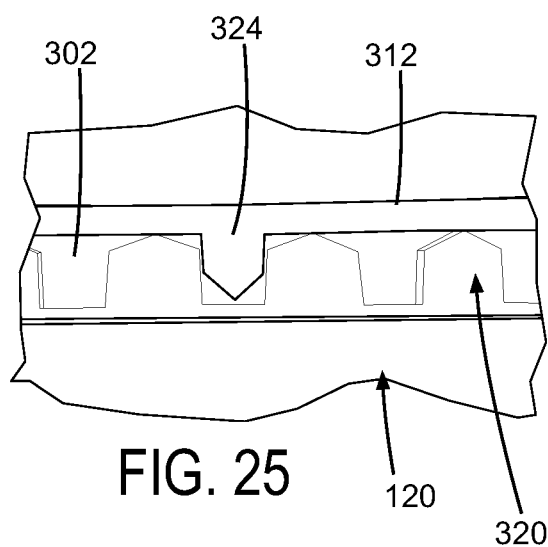
FIG. 25 is a partial, cross-sectional view showing details of the coupling of the circumferential wall of FIG. 23 with the wall member of FIG. 24.

Dosing component 103 is rotationally locked with coupling component during dose setting. As previously indicated, this may be accomplished by way of a variety of locking mechanisms. Illustratively, coupling wall 112 is received in the gap between inner wall 114 and outer wall 120. As described, the locking mechanism may comprise mechanical features, such as teeth 164 received within slots 162 (FIG. 9), or complementary shaped, mutually-facing teeth extending axially from the coupling and dosing components (FIG. 25). As these examples demonstrate, the teeth in either event may, for example, be formed on the coupling wall of the coupling component and one of the inner and outer walls of the dosing component. In a further aspect, to reduce the risk of damage to the medication delivery device, the locking mechanism is configured to cause disengagement of the dosing component from the coupling component in the event that a rotational force is applied from the dosing component to the coupling component in excess of a predetermined amount.

Illustratively, the locking mechanism is configured also to allow for disengagement upon axial movement of the dosing component toward the coupling component. Once disengaged, the coupling component is free to rotate relative to the dosing component. As also described, axial movement of the actuator in the direction of the dose setting member results in clutch 44 disconnecting the rotational engagement of the actuator with the dose setting member. In one aspect, pressing the housing assembly 100 moves dosing component 103 closer to coupling component 101 and coupling component 101 is thereby rotationally disengaged from dosing component 101. This occurs before actuator 34 moves a sufficient distance to initiate dose delivery. In another aspect, a wake-up switch is provided to cause relevant components of electronics assembly 140 to activate in time to detect the dose delivery. In another aspect, pressing housing assembly 100 disengages dosing component 103 from coupling component 101 and engages the wake-up switch, and subsequent distal movement presses dose button 42 and dose delivery occurs.

As shown, although not required, the disengagement of dosing component 103 from coupling component 101 may occur such that there is no contact between those two components once disengaged. For example, referring to FIG. 14 the upper end of coupling wall may be spaced apart from the interior of distal wall portion 119. Providing such a space avoids contact between coupling wall 112 and outer wall 120 which could otherwise provide frictional resistance to rotation of coupling component 101 relative to dosing component 103 during dose delivery.

In the second mode of module 20, the locking mechanism is disengaged, and first and second housing portions 102, 104 are rotatable relative to each other. An axial movement or compression of second housing portion 104 relative to first housing portion 102 is operative to transition module 20 from the first mode to the second mode by disengaging the locking mechanism to allow relative rotation of first and second housing portions 102, 104 about the longitudinal axis of module 20. In particular, the axial movement of second housing portion 104 towards first housing portion 102 causes teeth 164 to axially slide out of corresponding slots 162 to rotationally uncouple first and second housing portions 102, 104.

In general, dosing component 103 has a second operating mode during dose delivery in which coupling component 101 is rotatable relative to the dosing component 103. In this second mode, dosing component 103 is axially and rotationally fixed to actuator 34. Dosing component 103 is axially fixed in that the dosing component bears against actuator 34 as the housing assembly 100 is pressed distally to deliver a dose. Further, dosing component 103 is rotationally fixed to actuator 34 either by a frictional engagement or by other locking means as previously described. During dose delivery, actuator 34, including dose button 42, is pressed by the user and translates axially, while being held from rotating relative to device body 11. Since clutch 44 has released the rotational connection between actuator 34 and dose setting member 32, the dose setting member spirals back into device body 11.

Figure 13:
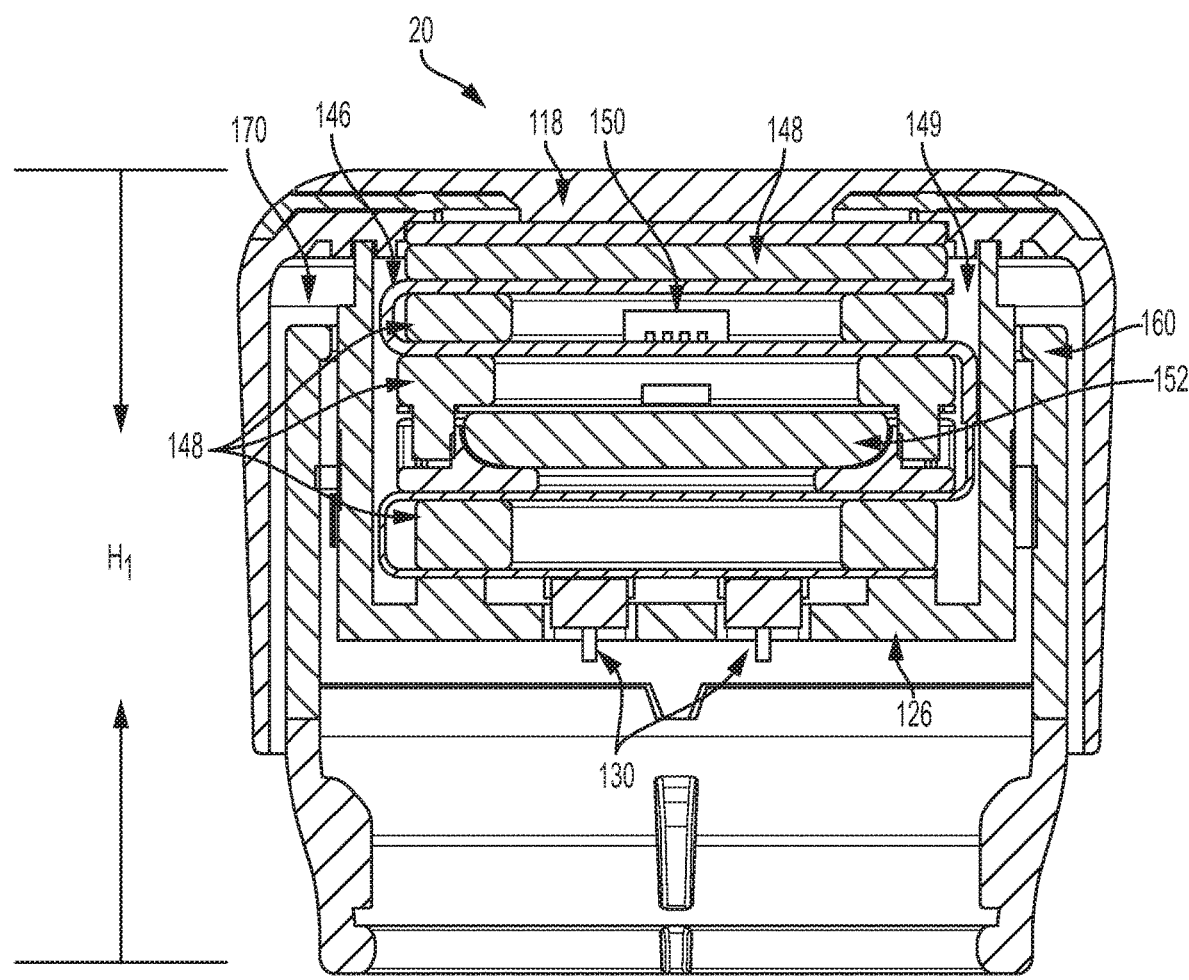
FIG. 13 is a side view in longitudinal cross-section of the dose detection module of FIG. 6 removed from a delivery device, wherein the dose detection module is in a first operating mode corresponding to a dose setting operation of a medication delivery device.

FIG. 13 illustrates dose detection module 20 in the first operating mode with first and second housing portions 102, 104 rotationally locked together by the locking mechanism and at an axially home position. In the first mode, the overall height of module 20 is a first height $H_1$, and a gap 170 extends between lip 160 and end wall 118, as illustrated in FIG. 13. In the first mode with module 20 coupled to delivery device 10, a rotational or screw force on module 20 (such as applied to outer wall 120 or any other user accessible portion) causes corresponding rotation and axial motion of dose setting member 32 to operate delivery device 10 in the dose setting mode described herein.

Figure 14:
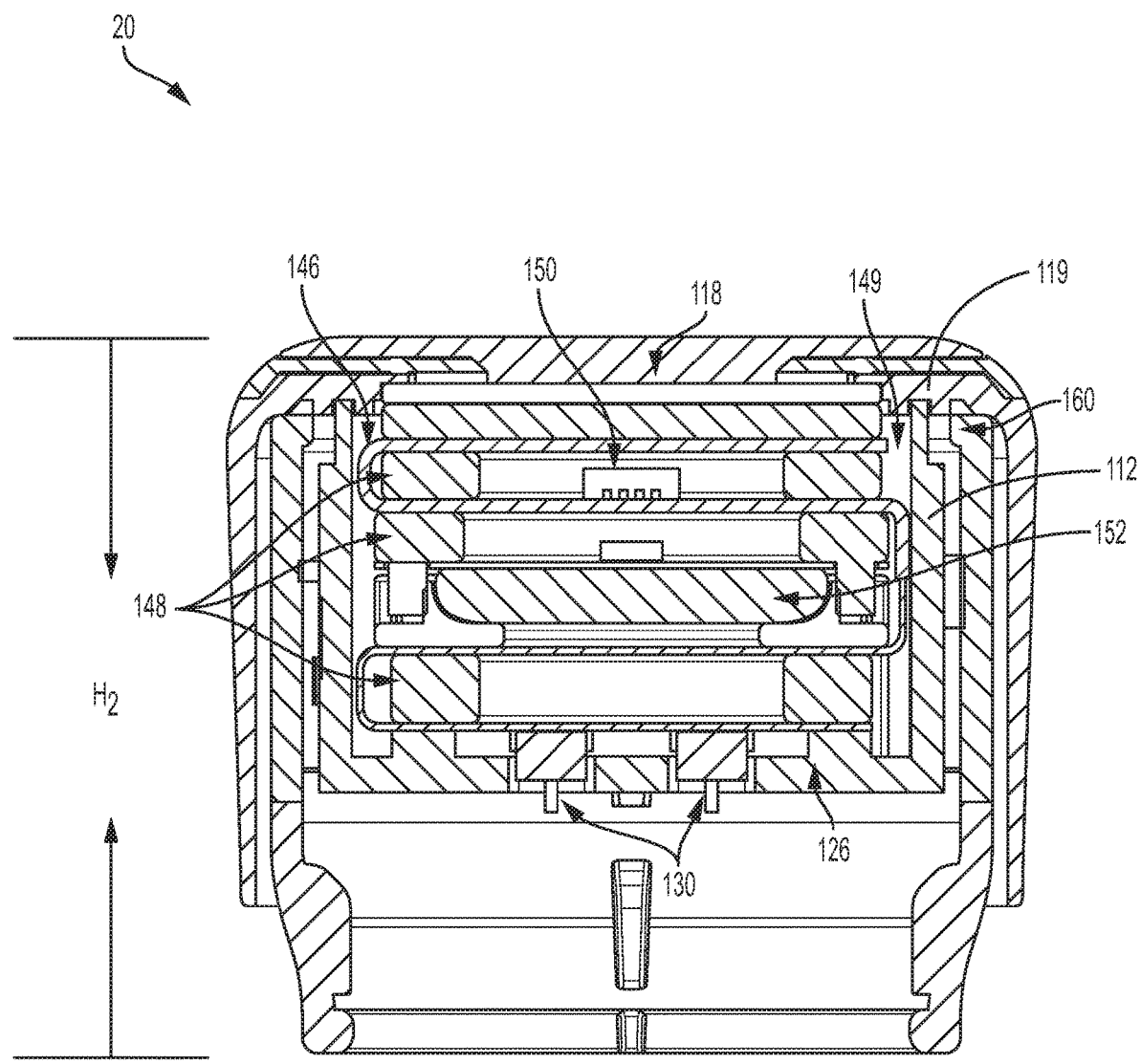
FIG. 14 is a side view in longitudinal cross-section of the dose detection module of FIG. 6 removed from a delivery device, wherein the dose detection module is in a second operating mode corresponding to a dose dispensing operation of a medication delivery device.

FIG. 14 illustrates dose detection module 20 in the second operating mode with second housing portion 104 compressed towards first housing portion 102 by an axial force to disengage the rotational locking mechanism. In the second mode, the overall height of module 20 is a second height H2 that is less than the first height $H_1$, and gap 170 is reduced or eliminated between lip 160 of coupling wall 112 and end wall 118 of cap portion 116, as illustrated in FIG. 14. In the second mode with module 20 coupled to delivery device 10, the axial force which compresses module 20 is transferred to actuator 34 to compress button 42 and thereby rotationally disengage actuator 34 from dose setting member 32, causing dose setting member 32 to screw back into housing to operate delivery device 10 in the dose dispensing mode. During the dose dispensing operation of delivery device 10, first housing portion 102 screws (moves axially and rotationally) with dose setting member 32 while second housing portion 104 remains rotationally fixed while moving only axially with dose setting member 32.

Figure 11:
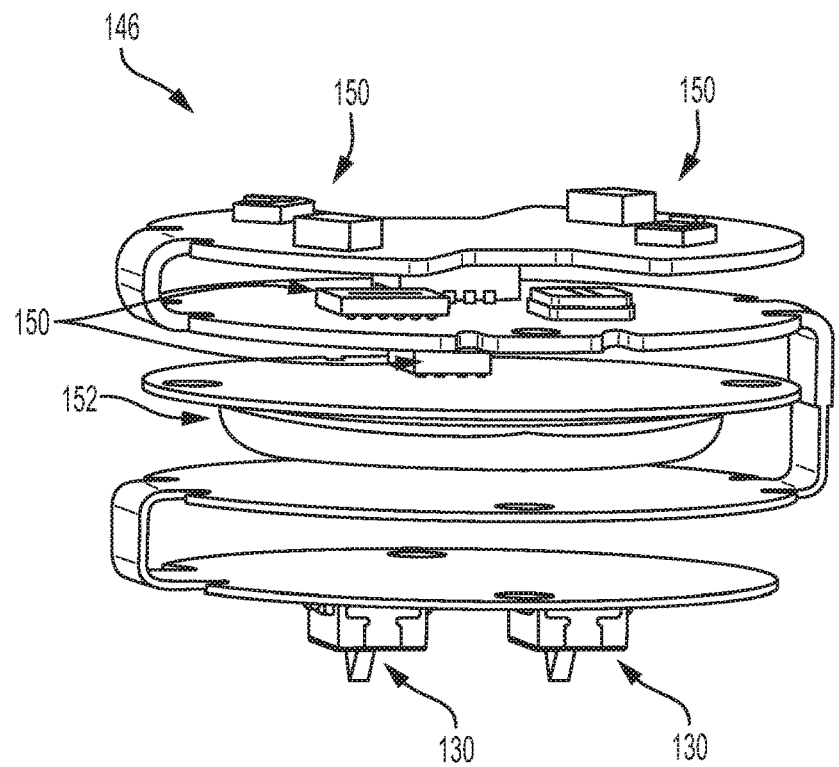
FIG. 11 is a side perspective view of a flexible printed circuit board (FPCB) of an electronics assembly of the dose detection module of FIG. 6.
Figure 12:
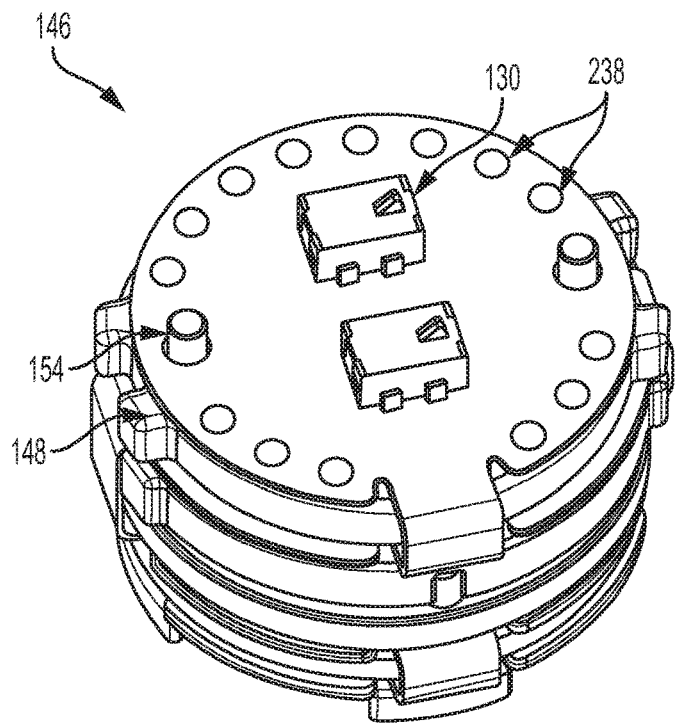
FIG. 12 is a bottom perspective view of the flexible printed circuit board (FPCB) of FIG. 11.

Referring to FIGS. 11 and 12, a flexible printed circuit board (FPCB) 146 of electronics assembly 140 is illustrated having a plurality of electronic components 150 disposed on each of a plurality of sections, each section comprising a single- or multi-layer circuit board. Electronic components 150 include light-emitting diodes (e.g., disposed on the top section for illuminating light pipes 144), a microcontroller unit (MCU) (e.g., including at least one processor core and memory), a communication device including a wireless transmitter/transceiver, an integrated real-time clock with power-on management circuit, etc., as described herein with respect to FIG. 15. A battery 152, illustratively a coin cell battery, is provided for powering components of FPCB 146. Each section or leaf of FPCB 146 is separated by a non-conductive spacer 148 (FIG. 12) to space apart the FPCB sections and electrical components. As illustrated in FIG. 12, a pair of alignment posts 154 extends from the distal end of FPCB 146 for rotationally aligning FPCB 146 to base wall 126 of drum 113.

Referring to FIGS. 13 and 14, FPCB 146 of electronics assembly 140 is shown housed in an interior space or compartment 149 formed by inner wall 114, base wall 126, and cap portion 116 of second housing portion 104. FPCB 146 is illustratively coupled at a distal end to base wall 126 and at a proximal end to end wall 118 of cap portion 116. Electrical switches 130 extend through base wall 126 and frictional pad 142 (FIG. 5) for engagement with button 42 of delivery device 10, as described herein.

Figure 15:
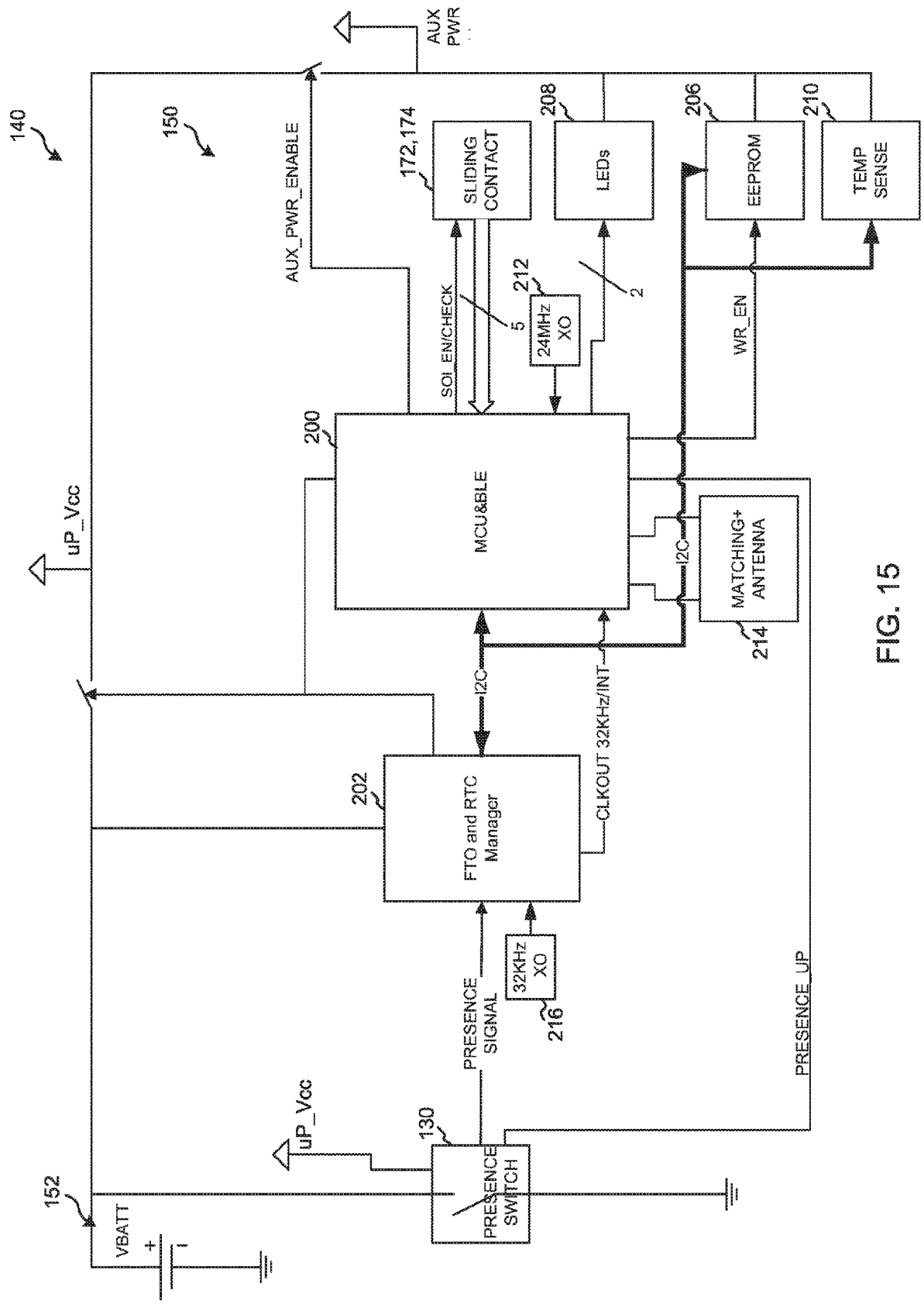
FIG. 15 is an electrical schematic of an electronics assembly according to an illustrative embodiment including a rotational sensing system.

FIG. 15 illustrates an exemplary electrical schematic of electronics assembly 140. In one embodiment, each component 150 illustrated in FIG. 15 with the exception of sliding contacts 172, 174 is coupled directly to FPCB 146 and is powered by battery 152, although other suitable physical configurations may be provided. Electronics assembly 140 includes a microcontroller unit (MCU) 200 comprising at least one processing core and internal memory. MCU 200 includes control logic operative to perform the operations described herein including detecting a dose delivered by delivery device 10 based on a detected relative rotation of first and second housing portions 102, 104 during the dose dispensing operation. MCU 200 is operative to store the detected dose in local memory (e.g., internal flash memory or on-board EEPROM 206). MCU 200 is further operative to wirelessly transmit a signal representative of the detected dose to a paired remote electronic device, such as a user's smartphone, over a Bluetooth low energy (BLE) or other suitable short or long range wireless communication protocol. Illustratively, the BLE control logic and MCU 200 are integrated on a same circuit.

MCU 200 is in communication with a pair of LEDs 208 for controlling illumination of indicator light 122, with EEPROM 206 for storing and/or reading data, and with a temperature sensor 210 for monitoring a temperature of module 20. A clock signal (e.g., 20 MHz) is provided to MCU 200 by clock generator 212 for synchronization. MCU 200 is operative to pair to the remote electronic device and transmit status and dose information signals to the remote device via antenna 214 using BLE protocol.

An integrated real-time clock with first-time on power management (RTC/FTO) circuit 202 is provided on FPCB 146 for managing power up control of module 20, e.g., upon a first use from a powered off state. RTC/FTO circuit 202 communicates with MCU 200 and EEPROM 206 over inter-integrated circuit (I2C) protocol and synchronizes with MCU 200 using a clock signal from clock generator 216.

Electronics assembly 140 of FIG. 15 includes a rotation sensor operative to detect the relative rotation of coupling wall 112 and inner wall 114 during the dose dispensing operation of device 10 to detect the delivered dose amount. The rotation sensor of the illustrated embodiment includes a plurality of sliding electrical contacts 172, 174 in communication with MCU 200. Alternatively, other suitable rotational sensors may be provided, including optical, acoustic, magnetic, mechanical switches, or other suitable rotation sensors.

Figure 16:
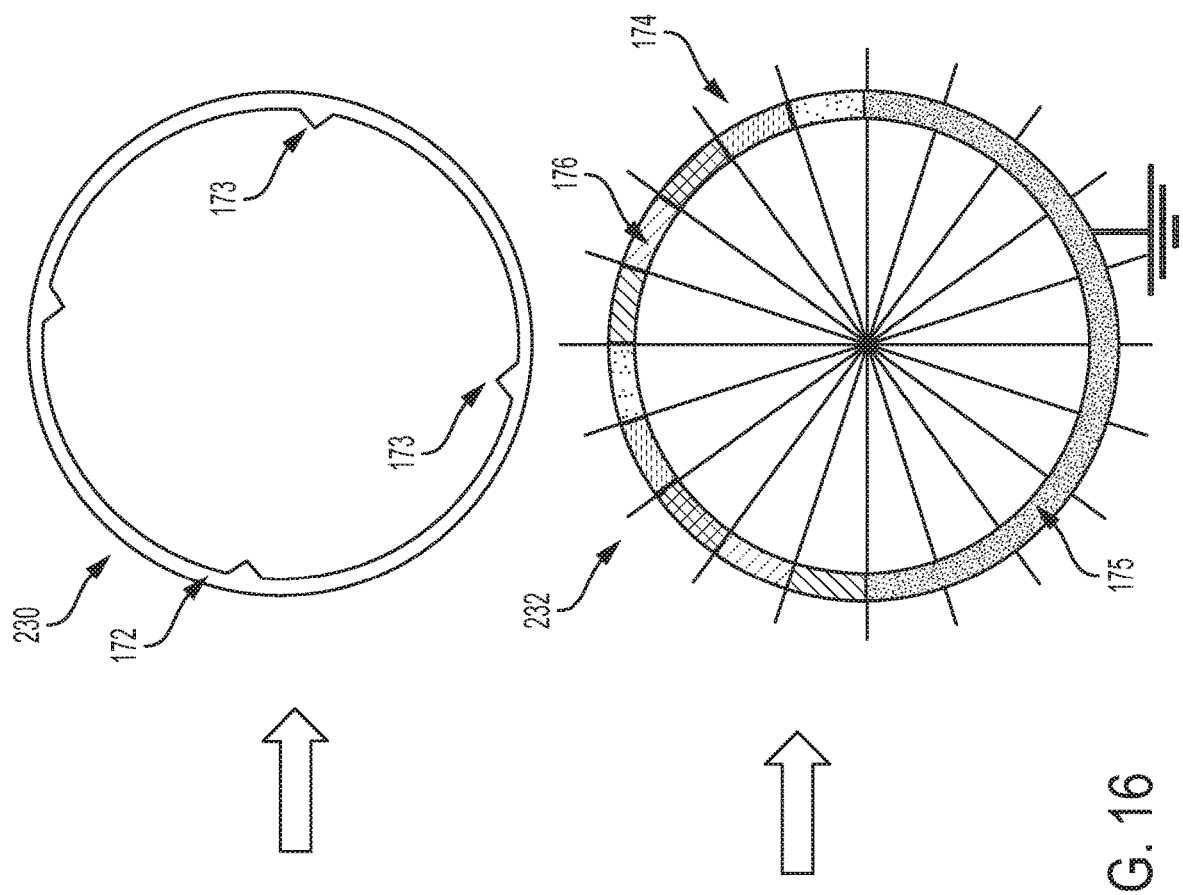
FIG. 16 is a partially exploded perspective view of circumferential walls of the dose detection module of FIG. 1 including sliding contacts and a conductive track, as well as schematic representations of the sliding contacts and the conductive track.
Figure 16:
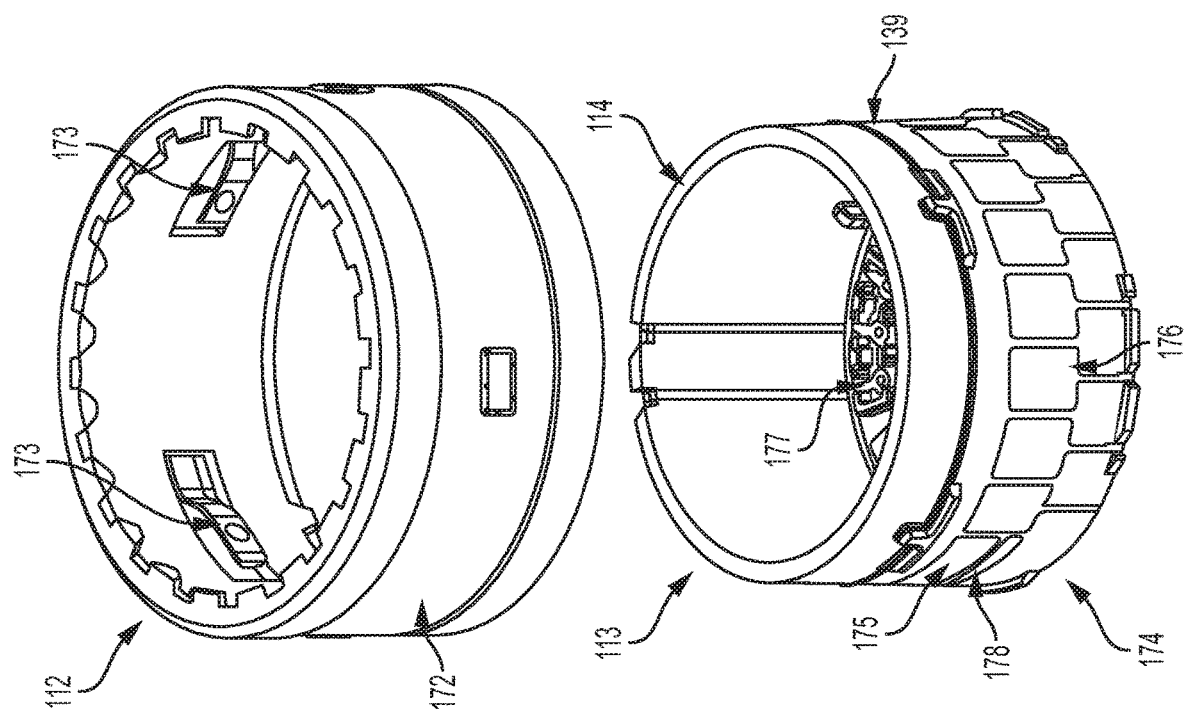

Referring to FIG. 16, a first set of electrical contacts in the form of a metal ring 172 is coupled to coupling wall 112 of first housing portion 102. Metal ring 172 is provided as a single conductor fixed around the outer periphery of wall 112 and including a plurality of equally spaced conductive sliding contact arms or points 173, illustratively four arms 173, extending through openings in coupling wall 112. All sliding contacts 173 of metal ring 172 are electrically connected together, as represented with the representative schematic 230 of metal ring 172. Similarly, a second set of electrical contacts 174 in the form of a conductive track 174 is disposed around lower wall portion 139 of inner wall 114 of second housing portion 104 and are in sliding engagement with contact arms 173 of metal ring 172. Accordingly, first and second contact sets 172, 174 are positioned in the gap that extends between walls 112, 114 (see FIG. 12). The conductive track 174 is comprised of a ground segment 175 extending around a first portion of the perimeter of inner wall 114 and a plurality of spaced conductive segments 176 extending around a second portion of the perimeter of inner wall 114. In the illustrative embodiment, ground segment 175 extends 180 degrees around the perimeter of inner wall 114 and conductive segments 176 extend the other 180 degrees around the perimeter of inner wall 114, as illustrated in FIG. 16 with representative schematic 232 of conductive track 174. Conductive segments 176 are spaced such that a non-conductive segment or portion of inner wall 114 extends between each segment 176 to provide electrical isolation between segments 176 to form the track 174.

Figure 17:
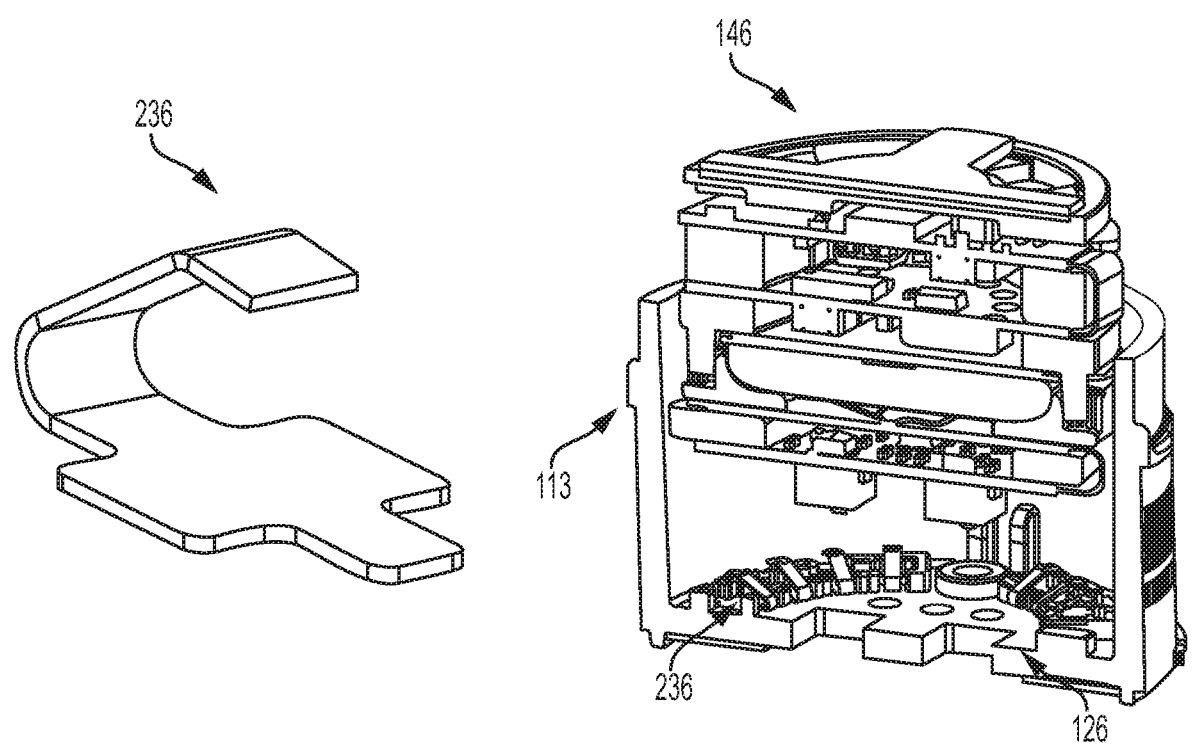
FIG. 17 is cross-sectional perspective view of the flexible printed circuit board (FPCB) of FIG. 11 positioned in a drum of the dose detection module of FIG. 1 for electrical coupling to a conductive track via spring contacts.

Conductive track 174 is illustratively coupled to an outer surface of wall portion 139 and includes connecting conductors 177 extending through openings in drum 113 to the interior of drum 113 for electrical coupling to FPCB 146. In the illustrative embodiment, each conductive segment 176 and ground segment 175 has at least one corresponding conductor 177 extending inside the wall portion 139. MCU 200 of electronics assembly 140 is in electrical communication with each conductor 177 for sensing the relative position of the sliding contacts 172, 174. Referring to FIG. 17, a plurality of spring contacts 236 are disposed around the interior bottom surface of base wall 126 and electrically connect conductors 177 to corresponding metal contact pads 238 (FIG. 12) of FPCB 146 for routing the rotational sensing lines to corresponding pins of MCU 200. In the illustrative embodiment, fourteen pairs of spring contacts 236 and contact pads 238 are provided corresponding to ten pairs for conductive segments 176 (for five sensing signals), two for ground segment 175, and two for a start of injection (SOI) conductive segment 178. Alternative contacts 236 may be provided, such as zebra connectors, pogo-pins, conductive tape, and soldered connections for example.

Figure 18:
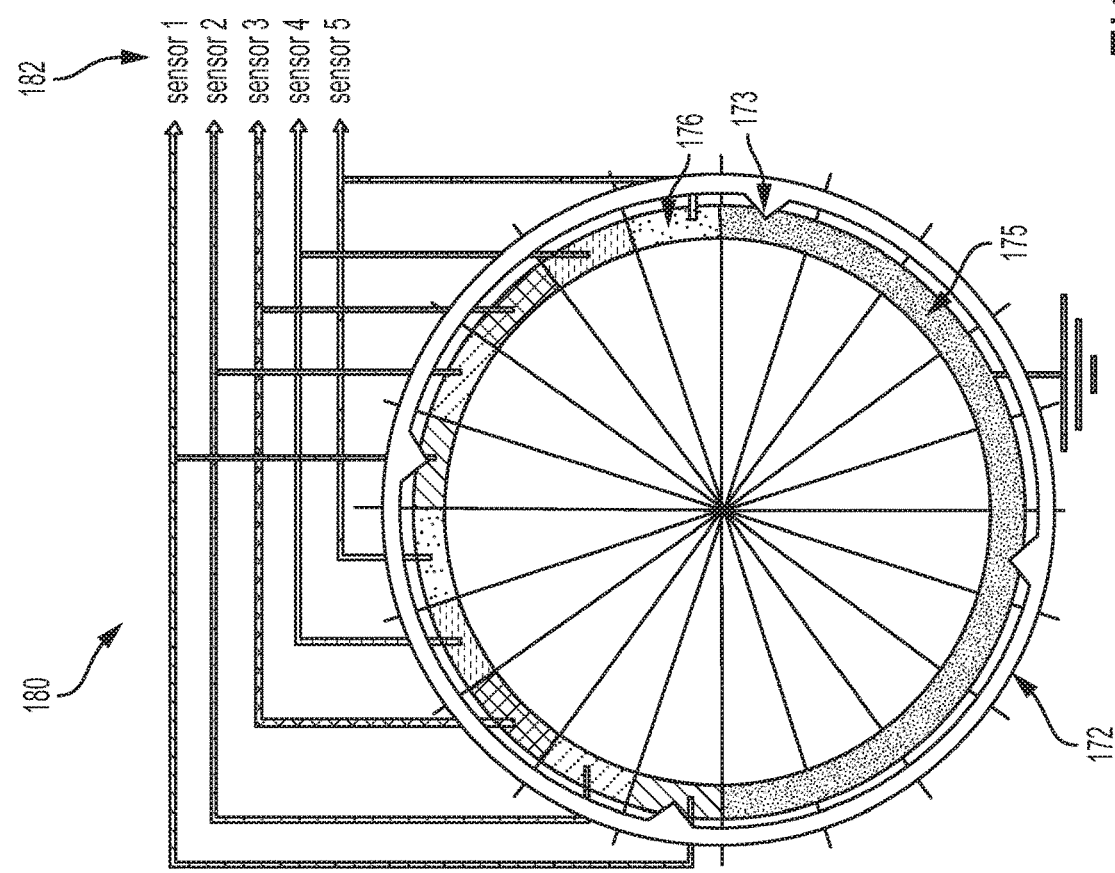
FIG. 18 is a schematic view of an exemplary rotational sensing scheme of the dose detection module according to an illustrative embodiment.

As illustrated with the representative schematic 180 of FIG. 18, sliding contacts 173 of first contact set 172 are spaced equally, illustratively 90 degrees apart, around the inner perimeter of wall 112 such that, at any rotational position of coupling wall 112 relative to inner wall 114, half of the total number of sliding contacts 173 (illustratively two sliding contacts 173) are engaged with the ground segment 175 and the other half of the total number of sliding contacts 173 (illustratively two sliding contacts 173) are engaged with the conductive track segments 176. In the illustrative embodiment, the portion of track 174 formed by conductive segments 176 includes two redundant conductive segment portions. In particular, conductive segments 176 include two sets of redundant segments spaced 90 degrees apart, wherein each corresponding segment pair represents a bit provided to a pin of MCU 200. As illustrated in FIG. 18, ten conductive segments 176 are provided for a five-bit system with two conductive segments 176 (one is redundant) for each bit. Accordingly, with the four contact arms 173 of coupling wall 112, track 174 has a resolution of 18 degrees corresponding to 20 different sensed rotational positions of coupling wall 112 relative to inner wall 114. The 20 different sensed relative rotational positions of walls 112, 114 correspond to the 20 different rotational incremental dose setting positions of dose setting member 32 described herein. Each bit pair of conductive segments 176 is in electrical communication with a corresponding sensor 182. Put another way, each sensor 182 is electrically coupled to two conductive segments 176 spaced 90 degrees apart, thereby providing bit redundancy and code repetition every five steps. In the illustrated embodiment, each sensor 182 includes an input pin of MCU 200.

Table 184 of FIG. 18 illustrates the exemplary coding scheme of the sliding contact system of the illustrative embodiment. For illustrative purposes, table 184 shows only the coding scheme for half of a full revolution (ten incremental positions) of contact ring 172 relative to conductive track 174, and the second half of the full revolution is a repetition of the coding scheme shown in table 184. The contact ring 172 shorts to ground a single sensor signal line at each of the five positions. As such, in this coding scheme, the bit corresponding to the pair of segments 176 engaged with the two contact points 173 has a logical value zero, while the remaining bits have a logical value of one. In table 184, each CODE column (one through five) corresponds to a sensor 182. When wall 112 is in a first rotational position with contact points 173 engaged with the pair of segments 176 coupled to the first sensor 182, the first bit changes to logical zero and the remaining bits remain logical one. When coupling wall 112 moves to a second rotational position with the same contact points 173 engaged with the segment pair 176 coupled to the second sensor 182, the first bit changes back to logical one, the second bit changes to logical zero, and the remaining bits stay at logical one. Accordingly, two bits change for each incremental change in the relative rotational position of walls 112, 114. In the illustrated embodiment, control logic of MCU 200 is operative to filter out unwanted bit sequences detected during transitions between bit states, such as bit sequences generated due to mechanical part tolerances and/or bouncing during bit state transitions.

In an alternative embodiment, conductive track 174 may provide a four-bit system with eight conductive segments 176 extending 180 degrees around wall 114 including four redundant conductive segments 176. Other suitable numbers of conductive segments 176 and corresponding bits, such as a three bit or six-bit system, may be provided.

Figure 19:
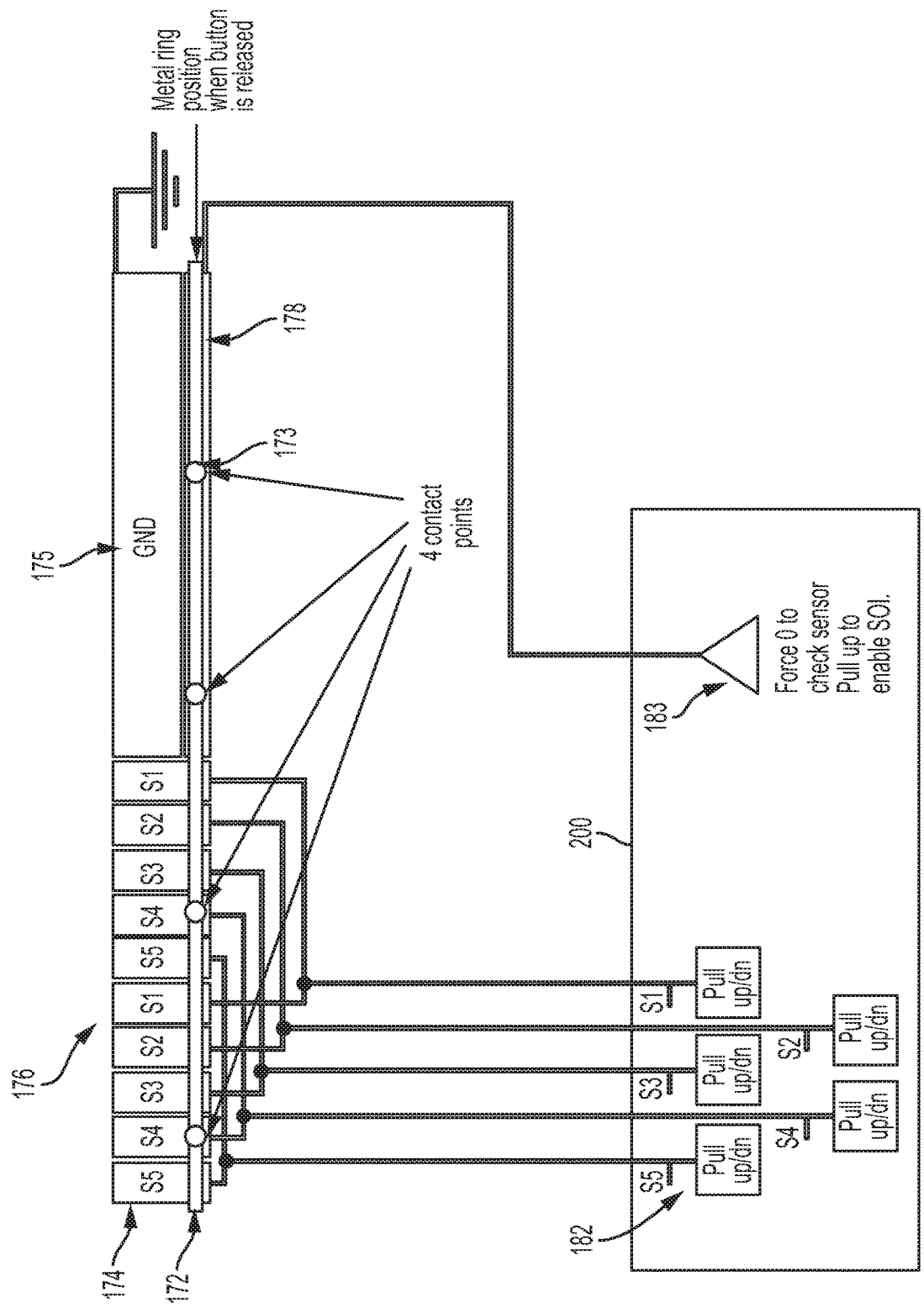
FIG. 19 is a schematic view of the exemplary rotational sensing scheme of FIG. 18 illustrating a sensor and contact arrangement when the dose detection module is in the first operating mode.
Figure 20:
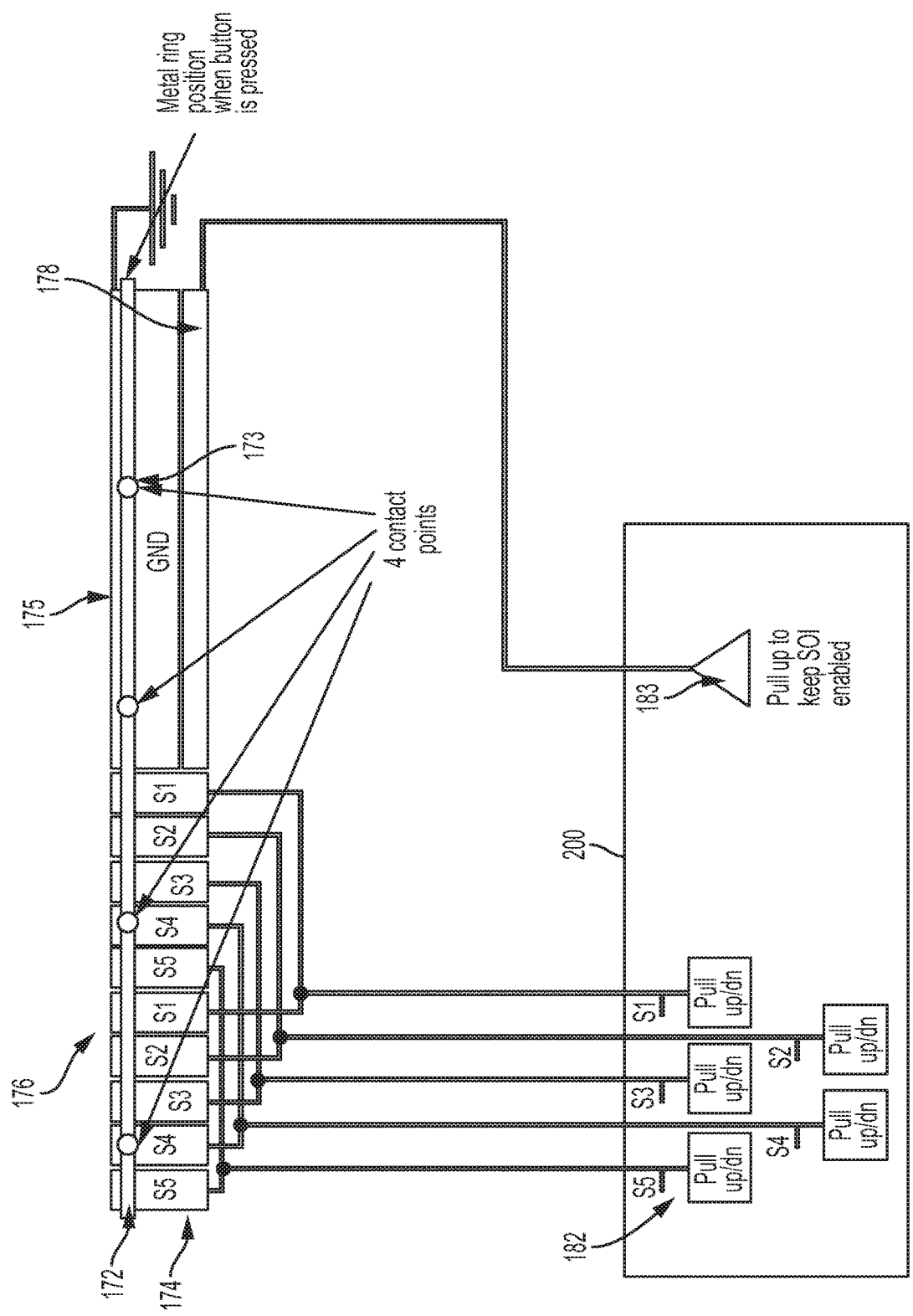
FIG. 20 is a schematic view of the exemplary rotational sensing scheme of FIG. 18 illustrating the sensor and contact arrangement when the dose detection module is in the second operating mode.

Referring to FIGS. 19 and 20, another schematic representation of the sliding contact system of FIG. 18 is illustrated. Conductive track 174 further includes a conductive segment 178 that is parallel to and axially offset from ground segment 175 and that extends the length of ground segment 175 (e.g., 180 degrees around wall 114). Conductive segment 178 serves as a start of injection (SOI) track and is used to distinguish between the first operating mode (dialing) and the second operating mode (injecting) of dose detection module 20. FIG. 19 illustrates the axial position of contact ring 172 in the first operating mode when second housing portion 104 is not axially compressed and is rotationally locked to first housing portion 102, i.e., prior to start of injection. In this mode, contact arms 173 of contact ring 172 engage conductive segment 178 but not ground segment 175. Conductive segment 178 is electrically connected to an input pin 183 of MCU 200 and normally is set high (logic 1) to enable start of injection detection. Each sensor input is also pulled high due to internal resistors of MCU 200 and segment 178 being disconnected from ground. When not in the injecting mode (when second housing portion 104 is not compressed), MCU 200 is operative to force pin 183 low (to ground), such as for periodically checking the five sensor inputs 182 and determining a relative rotational position based on one of the sensor inputs being shorted to ground.

FIG. 20 illustrates the axial position of contact ring 172 in the second operating mode when second housing portion 104 is axially compressed and is rotationally uncoupled from first housing portion 102. In the second mode, inner wall 114 moves axially relative to contact ring 172 such that two contact arms 173 of contact ring 172 engage ground segment 175 but not conductive segment 178. By transitioning the two contact arms 173 from segment 178 (normally at logic 1) to ground segment 175, one of the sensor inputs is shorted to ground and thereby MCU 200 detects the start of injection. In one embodiment, MCU 200 wakes up to a full power mode upon detecting start of injection. Accordingly, MCU 200 is operative to distinguish between the first and second modes of operation of dose detection module 20. After metal ring 172 transitions to the axial position shown in FIG. 20, module 20 is ready to count the rotational increment changes as coupling wall 112 rotates relative to inner wall 114 to detect the delivered dose of medication. In the illustrated embodiment, MCU 200 is configured to detect the relative rotation of housing portions 102, 104 by counting the sensor state changes which correspond to rotational increments of dose setting member 32 throughout the injection event. The total number of rotational increments corresponds to the amount of medication delivered by device 10. When metal ring 172 transitions back to segment 178, all sensor inputs are pulled high (logic 1) and MCU 200 thereby detects that the injection is complete.

Upon completion of an injection, pressure is removed from the module and contact ring 172 returns to the position shown in FIG. 19. In this position, the system is operable to continuously or occasionally detect the rotational position of second housing portion 104 relative to first housing portion 102 while the device is at rest. In particular, two of the contact arms 173 are engaged with conductive SOI segment 178 and the other two contact arms 173 are engaged with one pair of the sensor inputs S1-S5, which thereby provides an indication of the relative, at-rest rotational position of walls 112 and 114. The SOI track 178 is driven low by the processor which pulls low the sensor touched by the contact arms so that the sensor status can be checked in the resting position.

In one embodiment, the last resting position of a previous injection is taken as the first step for a new injection so that a jump in the first step may be captured and corrected if appropriate. If some steps are missed during rotation, or even the first or the last step, the SOI reading is used to recover the dose injected accurately. In this embodiment, because the SOI is only driven low at the end of the injection, no additional current consumption occurs.

Optionally, a slight increased diameter in correspondence with the resting position is put in place, such as by slightly increasing the diameter of the wall or SOI trace only at the resting position. This increases the likelihood of reliably reading the resting position without increasing the frictional torque between housing portions during injecting.

Referring again to FIG. 15, pen presence switches 130 are routed to an input of RTC/FTO circuit 202 for signaling the attachment of module 20 to pen 10. In one embodiment, one switch 130 is normally open (N.O.) and the other switch 130 is normally closed (N.C.). When module 20 is detached, a presence signal input of circuit 202 is low (logic 0) and module 20 remains powered off. When module 20 is attached to pen 10, the N.O. switch 130 closes and the N.C. switch 130 opens to output a presence signal to the input of circuit 202. In response to the pen presence signal, circuit 202 enables MCU 200 to power on. In one embodiment, in response to the signal MCU 200 powers on to a low power/deep sleep mode (e.g., 150 nA) and waits for detection of sliding contact movement before transitioning to fully powered on. In another embodiment, in response to the signal MCU 200 fully powers on before entering the low power mode (sleep state) after a predetermined period of inactivity (e.g., no detection of sliding contact movement). The pen presence signal may serve to avoid unwanted wake up of the system 140 when module 20 is not attached to the device 10 (i.e. due to an unwanted sliding contact movements during module 20 handling).

In one embodiment, RTC/FTO circuit 202 is always powered on (even in the powered-off mode of MCU 200) since circuit 202 has low power consumption. In one embodiment, whenever switches 130 are engaged MCU 200 is always at least in the low power mode. Module 200 is operative to go from the fully powered on mode to the low power mode under MCU 200 control (such as when module 200 is disconnected from device 10 and/or after a predetermined period of inactivity), and wake-up from this state is done by actuation of switches 130 or a detected transition of a sliding contact sensor.

Figure 21:
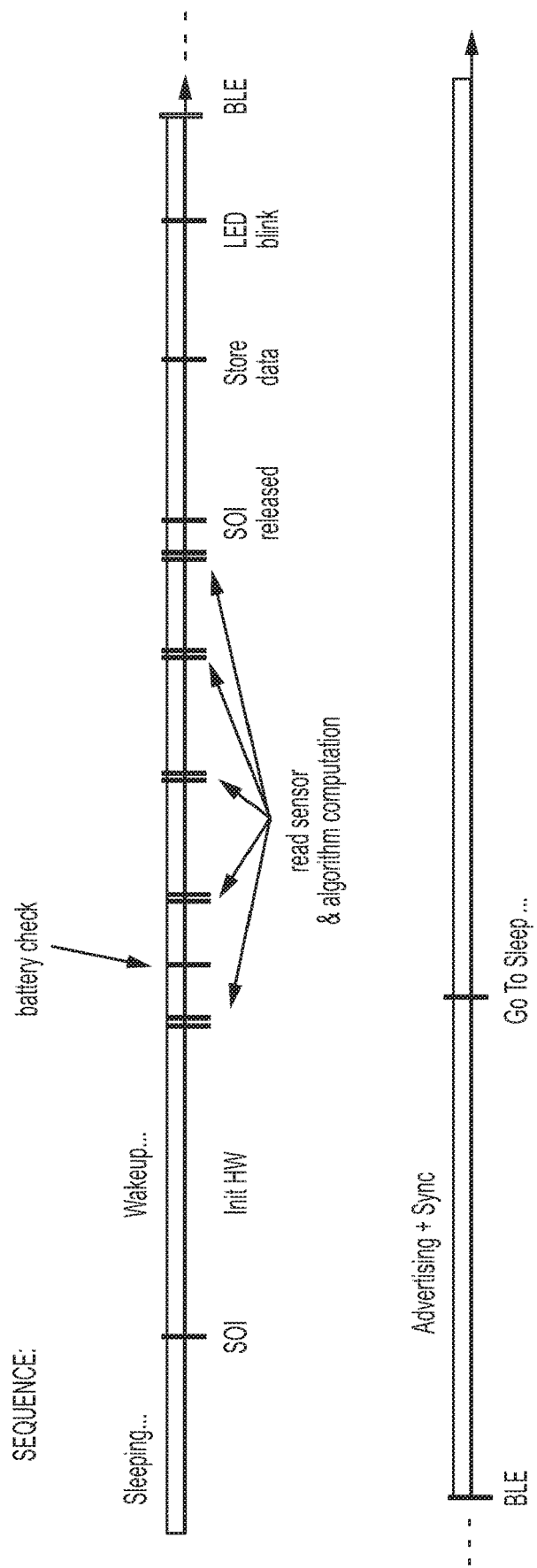
FIG. 21 is a sequence of operation of the electronics assembly of the dose detection module according to one exemplary embodiment.

FIG. 21 illustrates an exemplary sequence of operations of the electronics assembly 140 of FIG. 15.

In an exemplary mode of use for attachment of module 20 to device 10, the user aligns the visual alignment feature(s) of module 20 (e.g., feature 135 of FIG. 6) and device 10 and module 20 is snap fitted to dose setting member 32 of device 10. The locking mechanism (e.g., teeth 164 and slots 162) ensure proper alignment of the rotational sensor. When module 20 touches button 42 of device 10, the presence switches 130 trigger an MCU 200 power on from a powered off state. In one embodiment, any detection of false injection event during attachment is disregarded by MCU 200. When module 20 is powered on and ready to be used, indicator lights 122 signal green.

In an exemplary mode of use for dialing a dose, module 20 is rotated relative to housing 12 of device 10, and such rotation is translated to dose setting member 32 to screw dial member 36 up to the desired dose amount. In an illustrated embodiment, electronic module 20 is unaware of the dialing event since no signal variation is typically captured by module 20 during this phase.

In an exemplary mode of use for injecting a dose, cap portion 116 of module 20 is pushed relative to housing 12 to start injection. The axial force disengages the locking mechanism in module 20 and the clutch in delivery device 10, and first housing portion 102 is free to rotate relative to second housing portion 104 and dial member 36 is free to rotate relative to button 42 of device 10. The initial small relative axial movement of housing portions 102, 104 (during disengagement of the locking mechanism) some sensors will transition from logic 1 to logic 0 as soon as the contact arms 173 touch the ground pad 175, which wakes up the MCU 200 that will start booting/check/sensing monitoring. When injection ends, the user releases the cap portion 116, and MCU 200 captures the injection event until a certain timeout period following de-assertion of cap portion 116, stores the dose information, provides LED feedback (e.g., dose captured, transmitting, etc.), and starts BLE activity in order to automatically update the app running in the remote smartphone. In one embodiment, the BLE activity encompasses an advertising phase (with a Timeout of 30 sec) and a connection phase where relevant data are transmitted. In case of a transmission failure, manual sync of module 20 with the smartphone is possible later to transmit the dose information. Following transmission, module 20 transitions again to deep sleep state (low power mode).

In an exemplary mode of use for detaching module 20 from device 10, module 20 is detached by pulling module 20 with the required force away from device 10. In an illustrative embodiment, when module 20 is disconnected, the presence switches 130 will be de-asserted. In response, MCU 200 will prepare the system for a power off of MCU 200, and the powered off mode will be maintained until the next module 200 attachment to a device 10.

Figure 22:
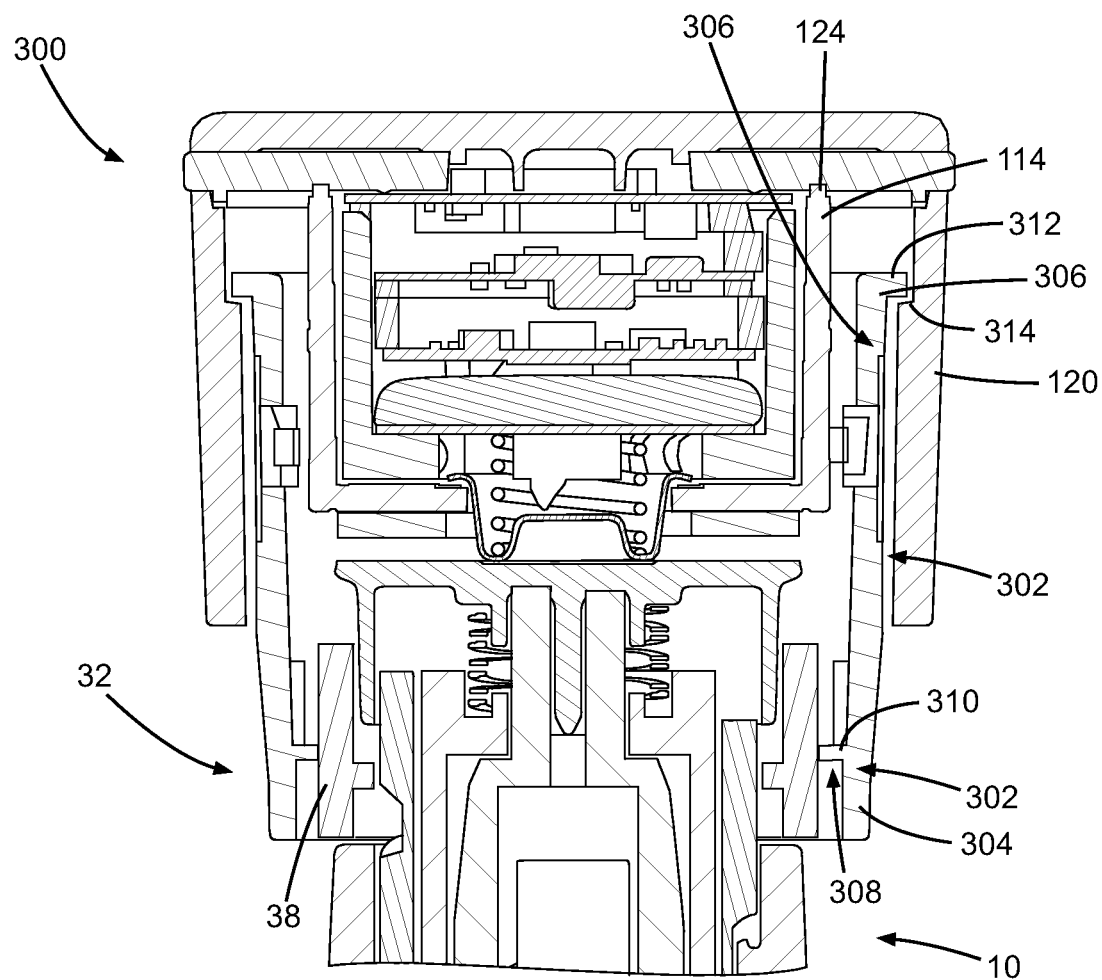
FIG. 22 is a cross-sectional view of an alternative dose detection module.

Referring to FIG. 22, a further illustrative embodiment of a module 300 is shown. In FIG. 22, module 300 includes a continuous wall member 302 extending from a lower portion 304 to an upper portion 306. Lower portion 304 is coupled with skirt 38. Lower portion 304 includes an annular ring portion 308 sized to engage an outer surface of dose setting member 32, illustratively skirt 38, for attaching lower portion 304 to delivery device 10. An inner surface 310 of lower portion 304 includes a plurality of surface features, illustratively variably sized projections and grooves, which are sized to engage corresponding surface features (e.g., grooves) of skirt 38 for coupling thereto, such as by a snap fit or an interference fit, although any other suitable fastening mechanism may alternatively be used to releasably couple lower portion 304 of wall member 302 to dose setting member 32. In the illustrative embodiment, the surface features provide mechanical keying of dose detection module 300 to delivery device 10.

Upper portion 306 of wall member 302 includes an outwardly-extending flange 312 which is received against an internal shoulder 314 of outer wall 120. When it is desired to remove module 300 from skirt 38 of the medication delivery device 10, the user pulls the module upwardly while grasping the body of the pen. The cooperation of flange 312 and shoulder 314 provides a firm, mechanical connection which transfers upward force on wall 120 of module 300 to separate the module from skirt 38. This avoids stress being applied to other portions of the module assembly, including for example the weld or frictional fit of inner wall 114 to mounting collar 124.

Figure 23:
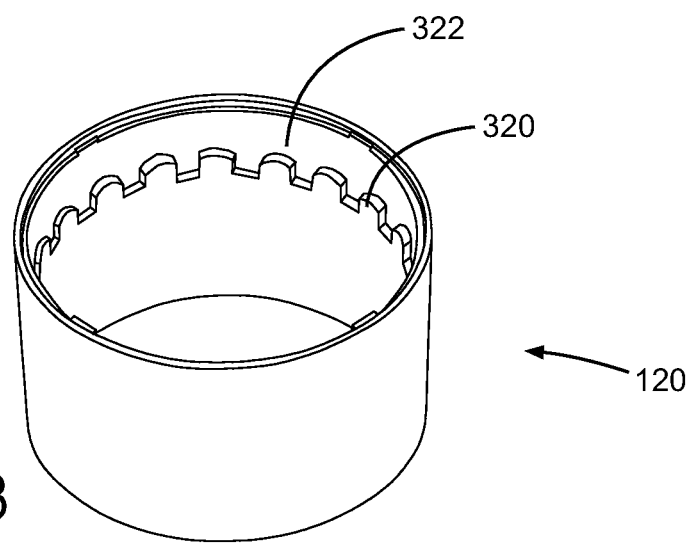
FIG. 23 is a perspective view of an illustrative form of a circumferential wall of a dose detection module.
Figure 24:
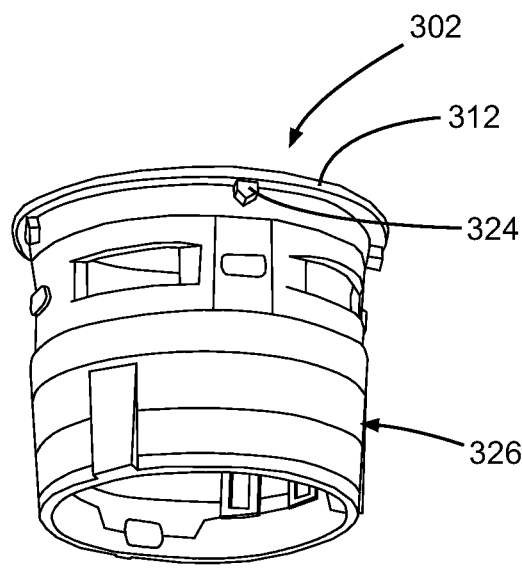
FIG. 24 is a perspective view of an illustrative form of a wall member of a dose detection module.

Referring to FIGS. 23-25, there is shown an illustrative coupling system between outer wall 120 and wall member 302. In FIG. 23 a perspective view of outer wall 120 is shown to include a series of upwardly-directed teeth 320 equally spaced around the interior surface 322. In FIG. 24 there is shown a perspective view of wall member 302. Wall member 302 includes a series of downwardly directed teeth 324 spaced around the exterior surface 326. Teeth 324 are shaped and positioned to be received within teeth 320 when wall member 302 is received within outer wall 120. Illustratively, outer wall 120 may include 20 teeth and wall member 302 may include four teeth, although other suitable configurations may be provided. The teeth are configured to readily mate upon movement together. For example, the teeth 324 are shaped such that they are received in any one of twenty discrete positions delineated by teeth 320, which may be provided to correspond to the discrete positions for setting the units of a medication dose.

During dose setting, outer wall 120 is spring-biased in the direction causing teeth 320 to engage with teeth 324. This rotationally couples together outer wall 120 and wall member 302, thereby coupling the dose setting member and the module. When the module is pushed to deliver a dose, the complementary teeth 320 and 324 separate, causing wall member 302 to uncouple from, and spin relative to, outer wall 120.

Referring to FIG. 25, further exemplary details as to the complementary teeth 320 and 324 are provided. Teeth 324 are shown in FIG. 25 in the coupling position such as exists during dose setting, and outer wall 120 is in its uppermost position relative to wall member 302. The engagement of the complementary teeth provides sufficient engagement in this condition to have rotation of outer wall 120 effect a dose setting. The larger surface area provided by the module facilitates this dose setting by the user. Excessive torqueing of the system is prevented by the cooperation of the complementary teeth. The teeth are configured to cause disengagement in the event that a rotational force is applied in excess of a predetermined amount. This disengagement may be caused to occur, for example, by providing tooth profiles which cause the angled end portions of teeth 324 to ride up along the angled end portions of teeth 320, thereby moving wall member 302 axially away from outer wall 120. The angled end portions of teeth 324 and teeth 320 also guide the re-engagement of teeth 324 with teeth 320 and ensure that they are engaged with each other as wall member 302 and outer wall 120 move axially back toward each other.

Illustratively, there is provided in a second aspect a dose detection module removably attachable to a medication delivery device. The medication delivery device includes a device body, a dose setting member, and an actuator. The dose setting member spirals relative to the device body during dose delivery in relation to the amount of dose delivery. The dose setting member also includes an exposed circumferential surface for use in rotating the dose setting member relative to the device body. The actuator spirals with the dose setting member during dose delivery and translates without rotation relative to the device body during dose delivery.

The module comprises a coupling component, a dosing component, and an electronics assembly. The coupling component is configured to be axially and rotationally fixed to the dose setting member. The dosing component has a first operating mode in which the dosing component is axially and rotationally fixed to the coupling component during a dose setting operation of the medication delivery device. The dosing component has a second operating mode in which the dosing component is axially and rotationally fixed to the actuator and the coupling component is rotatable relative to the dosing component. The electronics assembly includes a rotation sensor operative to detect rotation of the coupling component relative to the dosing component during dose delivery.

The module may be removably attached to the medication delivery device. While mounted to the medication delivery device, the module does not interfere with the normal operation of the device. However, the module provides a dosing component that is useful during dose setting to rotate the dose setting component, and which is useful during dose delivery to allow detection of relative rotation of the coupling component which is indicative of the amount of dose delivered.

The disclosed module and medication delivery device allow for an expedient method for determining dose delivery. Illustratively, there is disclosed a method of operating a medication delivery device of the type described herein. In particular, the medication delivery device includes a device body, a dose setting member, and an actuator. The dose setting member spirals relative to the device body during both dose setting and dose delivery, and includes an exposed circumferential surface for use in rotating the dose setting member relative to the device body. The actuator spirals with the dose setting member during dose setting and translates without rotation relative to the device body during dose delivery. The method comprises attaching a module to the medication delivery device, the module comprising a coupling component, a dosing component, and an electronics assembly. The coupling component includes a coupling surface configured to be attached to the exposed circumferential surface of the dose setting member, and the coupling surface is attached to the exposed circumferential surface to axially and rotationally fix the coupling component to the dose setting member.

The module is placed in a first operating mode with the dosing component axially and rotationally locked to the coupling component. The dosing component is rotated relative to the device body to thereby rotate the dose setting member to set a dose for delivery. The dosing component and the coupling component rotate and translate together during dose setting. The dosing component is then axially displaced a first distance in the distal direction toward the coupling component to place the module in a second operating mode. In the second operating mode, the coupling component is no longer rotationally locked to the dosing component, and the dosing component is axially and rotationally locked with the actuator. The dosing component is then axially displaced a further distance in the distal direction to deliver the dose. During dose delivery, the dose setting member and the coupling component rotate relative to the dosing component and the actuator. A rotation sensor is used to detect the rotation of the coupling component relative to the dosing component, and the amount of dose delivery is derived therefrom.

The invention claimed is:

1. A medication delivery device for detecting the amount of a drug dose delivery comprising:
   a device body;
   a dose setting member attached to said device body and rotatable about an axis of rotation relative to said device body, said dose setting member moving axially and rotating relative to said device body during dose setting and during dose delivery;
   an actuator attached to said device body, said actuator moving axially and rotating with said dose setting member relative to said device body during dose setting, said actuator moving axially and non-rotatably relative to said device body during dose delivery, said dose setting member rotating relative to said actuator during dose delivery in relation to the amount of dose delivered;
   a coupling component axially and rotationally fixed to said dose setting member;
   a dosing component having a first operating mode during dose setting in which said dosing component is axially and rotationally fixed to said coupling component, said dosing component having a second operating mode during dose delivery in which said coupling component is rotatable relative to said dosing component and in which said dosing component is axially and rotationally fixed to said actuator; and
   an electronics assembly including a rotation sensor operative to detect rotation of said coupling component relative to said dosing component during dose delivery.

2. The medication delivery device of claim 1 in which said coupling component is not in contact with said dosing component in the second operating mode.

3. The medication delivery device of claim 1 and further comprising a locking mechanism operative to rotationally lock said coupling component with said dosing component in the first operating mode.

4. The medication delivery device of claim 3 in which distal axial movement of said dosing component relative to said device body is operative to disengage the locking mechanism to allow rotation of said coupling component relative to said dosing component.

5. The medication delivery device of claim 4 in which distal axial movement of said dosing component relative to said device body is further operative to disengage said dose setting member from said actuator to allow rotation of said dose setting member relative to said actuator during dose delivery.

6. The medication delivery device of claim 3 in which said locking mechanism includes mutually-facing teeth extending axially from said coupling component and said dosing component.

7. The medication delivery device of claim 6 in which said dose setting member includes an exposed circumferential surface for use in rotating said dose setting member relative to said device body, said dosing component including an inner wall and an outer wall, said coupling component including a coupling wall received between the inner and outer walls, said coupling component extending distally beyond the inner wall and including a coupling portion attached to the exposed circumferential surface of the dose setting member.

8. The medication delivery device of claim 7 in which the mutually facing teeth are formed on the coupling wall of said coupling component and one of the inner and outer walls of said dosing component.

9. The medication delivery device of claim 1 comprising a module removably attached to said device body, said module including said dosing component, said coupling component, and said electronics assembly.

10. The medication delivery device of claim 1, wherein said device body includes a reservoir holding a medication.

11. A medication delivery device for detecting the amount of a drug dose delivery comprising:
    a device body;
    a dose setting member attached to said device body and rotatable about an axis of rotation relative to said device body, said dose setting member moving axially and rotating relative to said device body during dose setting and during dose delivery;
    an actuator attached to said device body, said actuator moving axially and rotating with said dose setting member relative to said device body during dose setting, said actuator moving axially and non-rotatably relative to said device body during dose delivery, said dose setting member rotating relative to said actuator during dose delivery in relation to the amount of dose delivered;
    a coupling component axially and rotationally fixed to said dose setting member;
    a dosing component having a first operating mode during dose setting in which said dosing component is axially and rotationally fixed to said coupling component, said dosing component having a second operating mode during dose delivery in which said coupling component is rotatable relative to said dosing component and in which said dosing component is axially and rotationally fixed to said actuator; and
    an electronics assembly including a rotation sensor operative to detect rotation of said coupling component relative to said dosing component during dose delivery, in which said dose setting member includes an exposed circumferential surface for use in rotating said dose setting member relative to said device body, said dosing component including an inner wall and an outer wall, said coupling component including a coupling wall received between the inner and outer walls, said coupling component extending distally beyond the inner wall and including a coupling portion attached to the exposed circumferential surface of the dose setting member.

12. The medication delivery device of claim 11 in which the outer wall extends distally to radially overlap at least a portion of the exposed circumferential surface of said dose setting member.

13. The medication delivery device of claim 11 in which the inner and outer walls of said dosing component are axially movable relative to the coupling wall of said coupling component.

14. The medication delivery device of claim 11 and further comprising a locking mechanism operative to rotationally lock said coupling component with said dosing component in the first operating mode.

15. The medication delivery device of claim 14 in which the locking mechanism is operative to rotationally lock the coupling wall of said coupling component with one of the inner and outer walls of said dosing component.

16. The medication delivery device of claim 11, wherein said device body includes a reservoir holding a medication.

17. A dose detection module removably attachable to a medication delivery device, the medication delivery device including a device body, a dose setting member, and an actuator, the dose setting member spiraling relative to the device body during dose delivery in relation to the amount of dose delivery, the dose setting member including an exposed circumferential surface for use in rotating the dose setting member relative to the device body, and the actuator spiraling with the dose setting member during dose setting and translating without rotation relative to the device body during dose delivery, said module comprising:
 a coupling component configured to be axially and rotationally fixed to the dose setting member;
 a dosing component having a first operating mode in which said dosing component is axially and rotationally fixed to said coupling component during a dose setting operation of the medication delivery device, and a second operating mode in which said dosing component is axially and rotationally fixed to the actuator and in which said coupling component is rotatable relative to said dosing component during a dose delivery operation of the medication delivery device; and
 an electronics assembly attached to said dosing component, said electronics assembly including a rotation sensor operative to detect rotation of said coupling component relative to said dosing component during dose delivery,
 in which said dosing component includes an inner wall and an outer wall, said coupling component including a coupling wall received between the inner and outer walls, said coupling component extending distally beyond the inner wall and including a coupling portion configured to be attached to the exposed circumferential surface of the dose setting member for attaching said coupling component to the dose setting member.

18. The module of claim 17 in which said coupling component is not in contact with said dosing component in the second operating mode.

19. The module of claim 17 and further comprising a locking mechanism rotationally locking said coupling component with said dosing component in the first operating mode, said locking mechanism including mutually-facing teeth extending axially from said coupling component and said dosing component, the teeth being configured to cause disengagement of said dosing component from said coupling component in the event that a rotational force is applied from said dosing component to said coupling component in excess of a predetermined amount.

20. The module of claim 17 in which the outer wall includes an inwardly-directed shoulder having a proximally-facing surface, the coupling wall including an outwardly-directed flange received adjacent the proximally-facing surface of the shoulder.

21. The module of claim 17 in which the outer wall extends distally to radially overlap at least a portion of the exposed circumferential surface of the dose setting member upon installation of said module onto the medication delivery device.

22. The module of claim 17, wherein said coupling component comprises a metal ring and said dosing component comprises a tracking ring disposed radially relative to the metal ring, said metal ring having a plurality of contacting arms disposed radially relative to and in contacting relationship with a conductive track disposed along the tracking ring.

23. The module of claim 22, wherein said metal ring is disposed radially outward of said tracking ring.

24. The module of claim 22, wherein said tracking ring includes a ground segment disposed along a first portion of a perimeter of the tracking ring, wherein the conductive track includes a plurality of spaced conductive segments extending along a second portion of the perimeter of the tracking ring.

25. The module of claim 24, wherein said first portion of the perimeter of the tracking ring is 180 degrees, and the second portion of the perimeter of the tracking ring is the other 180 degrees.

26. The module of claim 25, wherein the plurality of contacting arms are paired spaced equally around an inner perimeter of the metal ring such that at any rotational position of the tracking ring relative to the inner perimeter, half of a total number of contacting arms are engaged with the ground segment and the other half of the total number of contacting arms are engaged with the conductive segments.

27. The module of claim 17, further comprising a housing including a circumferential wall, a proximal end wall, and a distal base wall to abut with said actuator, wherein the electronics assembly includes at least one electrical switches, the electrical switches are positioned to be mechanically actuated with abutment between the distal base wall of the housing with said device actuator.

28. A method of operating a medication delivery device, the medication delivery device including a device body, a dose setting member, and an actuator, the dose setting member spiraling relative to the device body during dose delivery in relation to an amount of dose to be delivered, the dose setting member including an exposed circumferential surface for use in rotating the dose setting member relative to the device body, and the actuator spiraling with the dose setting member during dose setting and translating without rotation relative to the device body during dose delivery, said method comprising:
 attaching a module to the medication delivery device, the module comprising a coupling component, a dosing component, and an electronics assembly, the coupling component including a coupling surface configured to be attached to the exposed circumferential surface of the dose setting member and said attaching comprising attaching the coupling surface to the exposed circumferential surface to axially and rotationally fix the coupling component to the dose setting member;
 placing the module in a first operating mode with the dosing component axially and rotationally locked to the coupling component;
 rotating the dosing component relative to the device body to thereby rotate the dose setting member to set the amount of dose to be delivered, the dosing component and the coupling component rotating and translating together during dose setting;
 axially displacing the dosing component, a first distance in the distal direction toward the coupling component to place the module in a second operating mode with the coupling component rotationally unlocked from the dosing component and with the dosing component axially and rotationally locked with the actuator;
 axially displacing the dosing component, a further distance in the distal direction to deliver the amount of dose, the dose setting member and the coupling component rotating relative to the dosing component and the actuator during dose delivery; and determining the dose delivery based on the rotation of the coupling component relative to the dosing component during dose delivery.

29. The method of operating a medication delivery device of claim 28, in which said dosing component includes an inner wall and an outer wall, said coupling component including a coupling wall received between the inner and outer walls, said coupling component comprising a coupling portion extending distally beyond the inner wall and the coupling portion including the coupling surface.

\* \* \* \* \*